United States Patent
Kaib et al.

(10) Patent No.: US 12,053,274 B2
(45) Date of Patent: *Aug. 6, 2024

(54) DEVICE ADMINISTERED TESTS AND ADAPTIVE INTERACTIONS

(71) Applicant: ZOLL Medical Corporation, Chelmsford, MA (US)

(72) Inventors: Thomas E. Kaib, Irwin, PA (US); Patrick Hresko, Mount Pleasant, PA (US); Grace Owens, Cincinnati, OH (US); Trisha A. Biel, Glenshaw, PA (US); John Clark, Pittsburgh, PA (US); Melissa Smith, Pittsburgh, PA (US); Mark F. Roberto, Pittsburgh, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 311 days.

This patent is subject to a terminal disclaimer.

(21) Appl. No.: 17/401,660

(22) Filed: Aug. 13, 2021

(65) Prior Publication Data

US 2021/0369144 A1 Dec. 2, 2021

Related U.S. Application Data

(63) Continuation of application No. 15/374,238, filed on Dec. 9, 2016, now Pat. No. 11,116,426.

(Continued)

(51) Int. Cl.
*A61N 1/372* (2006.01)
*A61B 5/00* (2006.01)
(Continued)

(52) U.S. Cl.
CPC .......... *A61B 5/1125* (2013.01); *A61B 5/0022* (2013.01); *A61B 5/0205* (2013.01);
(Continued)

(58) Field of Classification Search
CPC .............. A61N 1/36014; A61N 1/3603; A61N 1/36031; A61N 1/3605; A61N 1/36128;
(Continued)

(56) References Cited

U.S. PATENT DOCUMENTS

| 4,674,330 A | 6/1987 | Ellis |
| 4,928,690 A | 5/1990 | Heilman et al. |

(Continued)

OTHER PUBLICATIONS

El-Kateb et al., "Can finger pinch strength be used as an alternative to hand grip strength for assessing muscle weakness in haemodialysis patients", Nephrology Dialysis Transplantation, May 2015, pp. iii337-iii338, vol. 30:3.

(Continued)

*Primary Examiner* — Eugene T Wu
(74) *Attorney, Agent, or Firm* — The Webb Law Firm

(57) ABSTRACT

An external medical device includes monitoring circuitry configured to monitor a cardiac condition of a patient using the external medical device; and a controller configured to: receive at least one of patient input and non-patient user input of a patient's ability; determine a patient interaction mode of the external medical device based on the at least one of the patient input and the non-patient user input; and adapt the patient interaction mode of the external medical device over time based on the at least one of the patient input and the non-patient user input.

26 Claims, 11 Drawing Sheets

Related U.S. Application Data

(60) Provisional application No. 62/265,093, filed on Dec. 9, 2015.

(51) Int. Cl.

| | |
|---|---|
| *A61B 5/0205* | (2006.01) |
| *A61B 5/11* | (2006.01) |
| *A61B 5/282* | (2021.01) |
| *A61N 1/39* | (2006.01) |
| *G16H 40/63* | (2018.01) |
| *G16H 40/67* | (2018.01) |
| *A61B 5/12* | (2006.01) |
| *A61B 5/22* | (2006.01) |
| *A61B 5/35* | (2021.01) |
| *A61N 1/00* | (2006.01) |
| *A61N 1/36* | (2006.01) |
| *G16H 15/00* | (2018.01) |
| *G16H 50/20* | (2018.01) |

(52) U.S. Cl.
CPC ........ *A61B 5/02055* (2013.01); *A61B 5/1118* (2013.01); *A61B 5/282* (2021.01); *A61B 5/6805* (2013.01); *A61N 1/37247* (2013.01); *A61N 1/3968* (2013.01); *G16H 40/63* (2018.01); *G16H 40/67* (2018.01); *A61B 5/1101* (2013.01); *A61B 5/123* (2013.01); *A61B 5/225* (2013.01); *A61B 5/35* (2021.01); *A61B 5/4088* (2013.01); *A61B 5/6831* (2013.01); *A61B 5/7275* (2013.01); *A61B 5/746* (2013.01); *A61B 2560/045* (2013.01); *A61N 1/00* (2013.01); *A61N 1/36031* (2017.08); *G16H 15/00* (2018.01); *G16H 50/20* (2018.01)

(58) Field of Classification Search
CPC ............ A61N 1/36132; A61N 1/36135; A61N 1/36142; A61N 1/37235; A61N 1/37247; A61N 1/37258; A61N 1/37264; A61N 1/39; A61N 1/3904; A61N 1/39046; A61N 1/3993; A61B 5/74–7495
See application file for complete search history.

(56) References Cited

U.S. PATENT DOCUMENTS

| | | |
|---|---|---|
| 5,078,134 A | 1/1992 | Heilman et al. |
| 5,535,321 A | 7/1996 | Massaro et al. |
| 5,741,306 A | 4/1998 | Glegyak et al. |
| 5,944,669 A | 8/1999 | Kaib |
| 6,065,154 A | 5/2000 | Hulings et al. |
| 6,253,099 B1 | 6/2001 | Oskin et al. |
| 6,280,461 B1 | 8/2001 | Glegyak et al. |
| 6,681,003 B2 | 1/2004 | Linder et al. |
| 8,271,082 B2 | 9/2012 | Donnelly et al. |
| 8,369,944 B2 | 2/2013 | Macho et al. |
| 8,676,313 B2 | 3/2014 | Volpe et al. |
| 9,352,166 B2 | 5/2016 | Sullivan et al. |
| 9,827,435 B2 | 11/2017 | Walker et al. |
| 2004/0199409 A1 | 10/2004 | Brown |
| 2008/0148150 A1 | 6/2008 | Mall |
| 2008/0200868 A1 | 8/2008 | Alberti et al. |
| 2008/0306560 A1 | 12/2008 | Macho et al. |
| 2012/0293323 A1 | 11/2012 | Kaib et al. |
| 2013/0325096 A1 | 12/2013 | Dupelle et al. |
| 2014/0025131 A1 | 1/2014 | Sullivan et al. |
| 2014/0043149 A1 | 2/2014 | Cowan et al. |
| 2014/0085081 A1 | 3/2014 | Brown et al. |
| 2014/0094865 A1 | 4/2014 | Walker et al. |
| 2014/0094866 A1 | 4/2014 | Walker et al. |
| 2014/0135598 A1 | 5/2014 | Weidl et al. |
| 2015/0039053 A1 | 2/2015 | Kaib et al. |
| 2015/0290469 A1 | 10/2015 | Sullivan et al. |
| 2016/0004831 A1 | 1/2016 | Carlson et al. |
| 2017/0021184 A1 | 1/2017 | Pavel et al. |
| 2017/0296107 A1 | 10/2017 | Reid et al. |

OTHER PUBLICATIONS

Leong et al., "Prognostic value of grip strength: findings from the Prospective Urban Rural Epidemiology (PURE) study", Lancet, Jul. 18, 2015, pp. 266-273, vol. 386.

Please press the button below when you can hear the tone.

YES

Sometimes people have trouble remembering things. If you do not know the answers to some of the next questions, that's okay. It's very normal. If you do know the answers, the questions may seem obvious.

What is the date today? _____ [ ] Correct  [ ] Incorrect / Not answered

What day of the week is it? _____ [ ] Correct  [ ] Incorrect / Not answered

What is the name of this place? _____ [ ] Correct  [ ] Incorrect / Not answered

What is your telephone number? _____ [ ] Correct  [ ] Incorrect / Not answered

What is your street address? _____ [ ] Correct  [ ] Incorrect / Not answered

How old are you? _____ [ ] Correct  [ ] Incorrect / Not answered

When were you born? _____ [ ] Correct  [ ] Incorrect / Not answered

Who is the President of the U.S. now? _____ [ ] Correct  [ ] Incorrect / Not answered Who was the past President before him? _____ [ ] Correct  [ ] Incorrect / Not answered What was your mother's maiden name? _____ [ ] Correct  [ ] Incorrect / Not answered Subtract 3 from 20, and keep subtracting from
each new number all the way down. _____ [ ] Correct  [ ] Incorrect / Not answered
(20-17-14-11-8-5-2)

Please rate the patient's ability with respect to each of the following categories on a scale from 1 (poor) to 10 (good).

Patient reading ability _____ [ ]

Patient hearing ability _____ [ ]

Patient motor skills _____ [ ]

Patient dexterity _____ [ ]

Patient mental/emotional status _____ [ ]

DEVICE ADMINISTERED TESTS AND ADAPTIVE INTERACTIONS

CROSS REFERENCE TO RELATED APPLICATIONS

This application is a continuation of U.S. patent application Ser. No. 15/374,238, filed Dec. 9, 2016, entitled "Device Administered Tests and Adaptive Interactions", which claims the benefit of U.S. Provisional Patent Application No. 62/265,093 filed Dec. 9, 2015, entitled "Device Administered Tests and Adaptive Interactions", the disclosure of each of which is hereby incorporated in its entirety by reference.

TECHNICAL FIELD

The present disclosure relates to an external medical device and, in some aspects, to an external medical device configured to evaluate patient function, ability, and/or skill generally and/or in connection with operating the external medical device, and optionally modify the operation of the device to conform to the patient's ability.

BACKGROUND

There are a wide variety of electronic and mechanical devices for monitoring and treating patients' medical conditions. In some examples, depending on the underlying medical condition being monitored or treated, medical devices such as cardiac pacemakers or defibrillators can be surgically implanted or connected externally to the patient. In some cases, physicians can use medical devices alone or in combination with drug therapies to treat patients' medical conditions.

External pacemakers and defibrillators (such as automated external defibrillators or AEDs) have significantly improved the ability to treat these otherwise life-threatening conditions. One of the most deadly cardiac arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia. Ventricular fibrillation can be treated by an implanted or external defibrillator.

External pacemakers and defibrillators operate by applying corrective electrical pulses directly to the patient's heart. For example, bradycardia can be corrected through the use of an implanted or external pacemaker device.

Medical monitoring devices are also available. For example, such devices operate by monitoring the patient's heart for treatable arrhythmias and, when a treatable arrhythmia is detected, the device applies corrective electrical pulses directly to the heart. Wearable pacing devices and/or defibrillators have been developed for a certain population of patients, e.g., those that may have recently experienced a heart attack, that are susceptible to heart arrhythmias and are at temporary risk of sudden death, or that are awaiting an implantable device.

SUMMARY

Typically, a patient is fit to these types of medical devices and receives training for operating and maintaining these medical devices when he or she first receives the device from a service representative. Involvement of the service representative and the patient's ability to operate the device can vary based on the patient's level of comfort with the technology, as well as the patient's understanding and grasp of functional concepts. Other factors, such as the patient's physical and mental capability to perform the tasks required to operate the device, also impact the patient's ability to operate the device.

Preferred and non-limiting aspects or embodiments of the present invention will now be described in the following numbered clauses:

Clause 1. An external medical device comprising: monitoring circuitry configured to monitor a cardiac condition of a patient using the external medical device; and a controller configured to: receive at least one of a patient input and a non-patient user input of a patient's ability; determine a patient interaction mode of the external medical device based on the at least one of the patient input and the non-patient user input; and adapt the patient interaction mode of the external medical device over time based on the at least one of the patient input and the non-patient user input.

Clause 2. The external medical device of clause 1, wherein the controller is configured to cause the external medical device to enter the determined patient interaction mode, and wherein the determined patient interaction mode is selected based on a technology comfort level of the patient as determined from the at least one of the patient input and the non-patient user input.

Clause 3. The external medical device of clause 1 or 2, wherein the determined patient interaction mode is selected from a) a first technology comfort mode, b) a second technology comfort mode, and c) a custom technology comfort mode.

Clause 4. The external medical device of any of clauses 1-3, wherein the first technology comfort mode is characterized by having predominantly more textual elements on an interface of the external medical device than the second technology comfort mode.

Clause 5. The external medical device of any of clauses 1-4, wherein the second technology comfort mode is characterized by having predominantly more image, animation, or video based elements on an interface of the external medical device than the first technology comfort mode.

Clause 6. The external medical device of any of clauses 1-5, wherein the custom technology comfort mode is configured by adjusting or customizing one or more features or functions of the external medical device based on the at least one of the patient input and the non-patient user input.

Clause 7. The external medical device of any of clauses 1-6, wherein the controller is configured to cause the external medical device to enter the determined patient interaction mode, wherein the entering the determined patient interaction mode comprises setting or changing one or more of the following features or functions of the external medical device: a) output features or functions of the external medical device, b) visual output features or functions of the external medical device, c) audio output features or functions of the external medical device, and d) tactile output features or functions of the external medical device.

Clause 8. The external medical device of any of clauses 1-7, wherein the output features or functions of the external medical device comprise at least one of the following: a) an order or a sequence of one or more alarms, alerts, or instructions issued by the external medical device, b) a type of the one or more alarms, alerts, or instructions issued by the external medical device, b) a frequency of occurrence of one or more alarms, alerts, or instructions issued by the external medical device, c) an escalation pattern of the one or more alarms, alerts, or instructions issued by the external medical device, and d) a response requested by the one or more alarms, alerts, or instructions issued by the external medical device.

Clause 9. The external medical device of any of clauses 1-8, wherein the visual output features of functions of the external medical device comprise at least one of the following: a) selection of one or more visual elements for an interface of the external medical device, b) an arrangement of the visual elements on the interface, b) an output display color of the one or more visual elements, c) an image or font display size of the one or more visual elements, and d) a display contrast of one or more visual elements or the interface.

Clause 10. The external medical device of any of clauses 1-9, wherein the audio output features of the external medical device comprise at least one of the following: a) selection of one or more audio output elements including one or more of a tone alarm or alert, a gong alarm or alert, a siren alarm or alert, or verbal messages, b) an order or sequence of the one or more audio elements provided by the external medical device, c) an audio output volume of the one or more audio output elements, d) a tonal frequency of the one or more audio output elements, and e) an escalation pattern of the one or more audio output elements.

Clause 11. The external medical device of any of clauses 1-10, wherein the tactile output features of the medical device comprise at least one of the following: a) selection of one or more tactile mechanisms including one or more of a continuous vibration, a pulsed vibration, or a mixed vibration, b) an order or sequence of the one or more tactile mechanisms provided by the external medical device, c) an intensity of the one or more tactile mechanisms, d) a frequency of vibration of the one or more tactile mechanisms, and e) an escalation pattern of the one or more tactile mechanisms.

Clause 12. The external medical device of any of clauses 1-11, wherein the controller is configured to provide a series of prompts during an initial patient interaction mode setting stage.

Clause 13. The external medical device of any of clauses 1-12, wherein the at least one of the patient input and the non-patient user input comprises responses from the patient and/or the non-patient user to the series of prompts during the initial patient interaction mode setting stage.

Clause 14. The external medical device of any of clauses 1-13, wherein the controller is configured to monitor a pattern of patient interactions with the external medical device over a period time or over a number of patient interactions with the external medical device and adapt the patient interaction mode of the external medical device over time by changing the patient interaction mode from a first one of a plurality of patient interaction modes to a second one of the plurality of patient interaction modes based on the monitored pattern of patient interactions.

Clause 15. The external medical device of any of clauses 1-14, wherein the controller is configured to monitor a pattern of patient interactions with the external medical device over a period time or over a number of patient interactions with the external medical device and adapt the patient interaction mode of the external medical device over time by changing one or more features or functions of the patient interaction mode of the external medical device based on the monitored pattern of patient interactions.

Clause 16. The external medical device of any of clauses 1-15, wherein the controller is configured to determine the patient interaction mode of the external medical device from a plurality of patient interaction modes.

Clause 17. The external medical device of any of clauses 1-16, wherein the controller is configured to adapt the mode of the external medical device over time by changing the patient interaction mode from a first patient interaction mode to a second patient interaction mode.

Clause 18. The external medical device of any of clauses 1-17, wherein the plurality of patient interaction modes comprise at least a first patient interaction mode, a second patient interaction mode, and a custom patient interaction mode, and wherein the first patient interaction mode is associated with patients having a different ability relating to the operation of the medical device than the second patient interaction mode.

Clause 19. The external medical device of any of clauses 1-18, wherein the controller is configured to determine the patient interaction mode as a custom patient interaction mode, and wherein, in the custom patient interaction mode, the controller is configured to adjust or customize one or more features or functions of the custom patient interaction mode of the external medical device based on the at least one of the patient input and the non-patient user input.

Clause 20. The external medical device of any of clauses 1-19, wherein the controller is configured to adapt the custom patient interaction mode of the external medical device over time by adjusting or customizing the one or more features or functions of the external medical device based on the at least one of the patient input and the non-patient user input.

Clause 21. The external medical device of any of clauses 1-20, wherein the controller is configured to adjust or customize at least one of the following features or functions of the external medical device: an audio output volume of the medical device, an audio output tonal frequency of the medical device, an output display color of the medical device, an image or font display size of the medical device, a display contrast of the medical device, a type of response requested by the output of the medical device, and a type of alarm, alert, or instruction issued by the medical device.

Clause 22. An external medical device comprising: monitoring circuitry configured to monitor a cardiac condition of a patient using the external medical device; and a controller configured to: receive at least one of a patient input and a non-patient user input of a patient's ability; and determine a patient interaction mode of the external medical device based on the at least one of the patient input and the non-patient user input.

Clause 23. The external medical device of clause 22, wherein the controller is configured to cause the external medical device to enter the determined patient interaction mode, and wherein the determined patient interaction mode is selected based on a technology comfort level of the patient as determined from the at least one of the patient input and the non-patient user input.

Clause 24. The external medical device of clause 22 or 23, wherein the determined patient interaction mode is selected from a) a first technology comfort mode, b) a second technology comfort mode, and c) a custom technology comfort mode.

Clause 25. The external medical device of any of clauses 22-24, wherein the first technology comfort mode is characterized by having predominantly more textual elements on an interface of the external medical device than the second technology comfort mode.

Clause 26. The external medical device of any of causes 22-25, wherein the second technology comfort mode is characterized by having predominantly more image, animation, or video based elements on an interface of the external medical device than the first technology comfort mode.

Clause 27. The external medical device of any of clauses 22-26, wherein the custom technology comfort mode is configured by adjusting or customizing one or more features or functions of the external medical device based on the at least one of the patient input and the non-patient user input.

Clause 28. The external medical device of any of clauses 22-27, wherein the controller is configured to cause the external medical device to enter the determined patient interaction mode, wherein the entering the determined patient interaction mode comprises setting or changing one or more of the following features or functions of the external medical device: a) output features or functions of the external medical device, b) visual output features or functions of the external medical device, c) audio output features or functions of the external medical device, and d) tactile output features or functions of the external medical device.

Clause 29. The external medical device of any of clauses 22-28, wherein the output features or functions of the external medical device comprise at least one of the following: a) an order or a sequence of one or more alarms, alerts, or instructions issued by the external medical device, b) a type of the one or more alarms, alerts, or instructions issued by the external medical device, c) a frequency of occurrence of one or more alarms, alerts, or instructions issued by the external medical device, d) an escalation pattern of the one or more alarms, alerts, or instructions issued by the external medical device, and e) a response requested by the one or more alarms, alerts, or instructions issued by the external medical device.

Clause 30. The external medical device of any of clauses 22-29, wherein the visual output features of functions of the external medical device comprise at least one of the following: a) selection of one or more visual elements for an interface of the external medical device, b) an arrangement of the visual elements on the interface, c) an output display color of the one or more visual elements, d) an image or font display size of the one or more visual elements, and d) a display contrast of the one or more visual elements for the interface.

Clause 31. The external medical device of any of clauses 22-30, wherein the audio output features of the external medical device comprise at least one of the following: a) selection of one or more audio output elements including one or more of a tone alarm or alert, a gong alarm or alert, a siren alarm or alert, or verbal messages, b) an order or sequence of the one or more audio elements provided by the external medical device, c) an audio output volume of the one or more audio output elements, d) a tonal frequency of the one or more audio output elements, and e) an escalation pattern of the one or more audio output elements.

Clause 32. The external medical device of any of clauses 22-31, wherein the tactile output features of the medical device comprise at least one of the following: a) selection of one or more tactile mechanisms including one or more of a continuous vibration, a pulsed vibration, or a mixed vibration, b) an order or sequence of the one or more tactile mechanisms provided by the external medical device, c) an intensity of the one or more tactile mechanisms, d) a frequency of vibration of the one or more tactile mechanisms, and e) an escalation pattern of the one or more tactile mechanisms.

Clause 33. The external medical device of any of clauses 22-32, wherein the at least one of the patient input and the non-patient user input comprises input to a series of prompts during an initial patient interaction mode setting stage of the external medical device.

Clause 34. The external medical device of any of clauses 22-33, wherein the patient input comprises input over a period of time during use of the external medical device by the patient after the initial patient interaction mode setting stage.

Clause 35. The external medical device of any of clauses 22-34, wherein the patient input comprises at least one of a response time of the patient input and a pattern of the patient input.

Clause 36. The external medical device of any of clauses 22-35, wherein the controller is configured to control an output component to provide an output to the patient, and wherein the output requests the patient input for determining an ability of the patient relating to one or more operations of the external medical device.

Clause 37. The external medical device of any of clauses 22-36, wherein the ability of the patient represents a function or skill of the patient relating to the one or more operations of the external medical device.

Clause 38. The external medical device of any of clauses 22-37, wherein the controller is configured to analyze the at least one of the patient input and the non-patient user input to generate a skill analysis representative of a level of skill of the patient relating to one or more operations of the external medical device.

Clause 39. The external medical device of any of clauses 22-38, wherein the skill analysis represents at least one of the following: an inductive reasoning level of the patient, an intelligence quotient level of the patient, a situation judgment level of the patient, a working memory level of the patient, a psychomotor level of the patient, a language level of the patient, a hearing level of the patient, a vision level of the patient, and a level of steadiness of a hand of the patient.

Clause 40. The external medical device of any of clauses 22-39, wherein the skill analysis represents a technology comfort level of the patient.

Clause 41. The external medical device of any of clauses 22-40, wherein the controller determines the patient interaction mode such that a number and/or type of features and/or functions of an interface of the external medical device is varied based on the technology comfort level of the patient.

Clause 42. The external medical device of any of clauses 22-41, wherein the controller is configured to provide the skill analysis as an output report to an output component of the external medical device, the output report providing at least one of a visual and an audible representation of the level of skill of the patient relating to the one or more operations of the external medical device.

Clause 43. The external medical device of any of clauses 22-42, wherein the controller is configured to analyze the at least one of the patient input and the non-patient user input to determine whether the patient is color blind.

Clause 44. The external medical device of any of clauses 22-43, wherein the controller is configured to determine the patient interaction mode of the external medical device from a plurality of patient interaction modes based on the skill analysis.

Clause 45. The external medical device of any of clauses 22-44, wherein the plurality of patient interaction modes comprise at least a first patient interaction mode, a second patient interaction mode, and a custom patient interaction mode, and wherein the first patient interaction mode is associated with patients having a different level of skill relating to the operation of the medical device than the second patient interaction mode.

Clause 46. The external medical device of any of clauses 22-45, wherein the controller is configured to determine the patient interaction mode as a custom patient interaction mode, and wherein, in the custom patient interaction mode, the controller is configured to adjust or customize one or more features or functions of the external medical device based on the at least one of the patient input and the non-patient user input.

Clause 47. The external medical device of any of clauses 22-46, wherein the controller is configured to adjust or customize at least one of the following features or functions: an audio output volume of the medical device, an audio output tonal frequency of the medical device, an output display color of the medical device, an image or font display size of the medical device, a display contrast of the medical device, a type of response requested by the output of the medical device, and a type of alarm, alert, or instruction issued by the medical device.

Clause 48. The external medical device of any of clauses 22-47, wherein the controller is configured to monitor a use of the external medical device by the patient over a period time or over a number of patient interactions with the medical device and receive or determine the patient input based on the monitored use.

Clause 49. The external medical device of any of clauses 22-48, wherein the controller is configured to determine or receive at least one of a response time of the patient input and a pattern of the patient input.

Clause 50. The external medical device of any of clauses 22-49, wherein the controller is configured to determine the patient interaction mode of the medical device by adjusting or modifying a type of an alarm, alert, and/or instruction issued by the medical device.

Clause 51. The external medical device of any of clauses 22-50, wherein the at least one of the patient input and the non-patient user input is at least one of determined or received before the patient operates or receives the medical device, determined or received on a periodic basis, and determined or received dynamically in response to patient interaction with the device.

Clause 52. The external medical device of any of clauses 22-51, wherein the at least one of the patient input and the non-patient user input represents at least one of the following: an inductive reasoning ability of the patient, an intelligence quotient of the patient, a situation judgment ability of the patient, a working memory ability of the patient, a psychomotor ability of the patient, a language ability of the patient, a technology ability of the patient, a color blindness of the patient, a hearing ability of the patient, a vision ability of the patient, and a steadiness of a hand of the patient.

Clause 53. The external medical device of any of clauses 22-52, wherein the determined patient interaction mode for the external medical device comprises at least one of a volume level and pitch of an alert, alarm, or instruction, a color and size of a displayed element, and a style of information provided on an output component.

Clause 54. The external medical device of any of clauses 22-53, wherein the controller is configured to determine at least one of the following: a respiration rate of the patient, a heart sound and movement of the patient, a lung sound and movement of the patient, a tissue fluid level of the patient, a blood pressure of the patient, a glucose level of the patient, and a blood oxygenation level of the patient.

Clause 55. The external medical device of any of clauses 22-54, comprising at least one of a cardiac monitor, a defibrillator, and a wearable defibrillator.

Clause 56. The external medical device of any of clauses 22-55 comprising a wearable external medical device.

Clause 57. The external medical device of any of clauses 22-56, wherein the wearable external medical device comprises a garment worn by the patient.

Clause 58. The external medical device of any of clauses 22-57, wherein the wearable external medical device comprises adhesive patches including at least one of sensing electrodes and therapy electrodes.

Clause 59. An external medical device comprising: a controller configured to receive assessment data, the assessment data representing at least one of a patient input and a non-patient user input of a patient's ability, wherein the controller is configured to process the assessment data to determine data representing an ability of the patient.

Clause 60. The external medical device of clause 59, wherein the controller is configured to provide a prompt to the non-patient user to select a patient interaction mode of the external medical device.

Clause 61. The external medical device of clause 59 or 60, wherein the non-patient user is one of a caregiver, a medical personnel, and a patient service representative.

Clause 62. The external medical device of any of clauses 59-61, wherein the controller is configured to control an output component to provide an output, wherein the output requests a response for determining the ability of the patient relating to one or more operations of the external medical device.

Clause 63. An external medical device comprising: monitoring circuitry configured to monitor a cardiac condition of a patient using the external medical device; and a controller configured to provide an output, wherein the output requests a response for determining an ability of the patient relating to one or more operations of the external medical device.

Clause 64. The external medical device of clause 63, wherein the controller is configured to control an output component to provide the output.

Clause 65. The external medical device of clause 63 or 64, wherein the controller is configured to control the output component to provide the output to the patient, wherein the output requests the response from the patient for determining the ability of the patient relating to the one or more operations of the external medical device.

Clause 66. The external medical device of any of clauses 63-65, wherein the output component comprises an interface configured to determine or receive the patient's response.

Clause 67. The external medical device of any of clauses 63-66, wherein the output component is configured to provide a plurality of different outputs to the patient that request a plurality of different patient responses.

Clause 68. The external medical device of any of clauses 63-67, wherein the controller is configured to determine the output provided to the patient from the plurality of different outputs based on a previous patient response to a previous output provided to the patient.

Clause 69. The external medical device of any of clauses 63-68, wherein the output component is configured to provide the output to the patient in response to a request from the patient or a non-patient user.

Clause 70. The external medical device of any of clauses 63-69, wherein the output requests the response from a non-patient user.

Clause 71. The external medical device of any of clauses 63-70, wherein the ability of the patient represents a function or skill of the patient relating to the one or more operations of the external medical device.

Clause 72. The external medical device of any of clauses 63-71, wherein the ability of the patient represents a level of the skill of the patient relating to the one or more operations of the external medical device.

Clause 73. The external medical device of any of clauses 63-72, wherein the controller is configured to determine or receive data representing the patient's response.

Clause 74. The external medical device of any of clauses 63-73, wherein the patient's response comprises at least one of a verbal response, a tactile response, and a movement of the external medical device by the patient.

Clause 75. The external medical device of any of clauses 63-74, wherein the controller is configured to determine or receive a non-patient user response including data representing a non-patient user observation of the patient.

Clause 76. The external medical device of any of clauses 63-75, wherein the output comprises substantially real-time output of an operation of the medical device during use of the external medical device by the patient.

Clause 77. The external medical device of any of clauses 63-76, wherein the use of the medical device by the patient comprises the patient wearing the external medical device.

Clause 78. The external medical device of any of clauses 63-77, wherein the controller is configured to determine or receive at least one of a response time of a patient's response to the output and a pattern of the patient's response to the output.

Clause 79. The external medical device of any of clauses 63-78, wherein the output comprises a test provided to the patient.

Clause 80. The external medical device of any of clauses 63-79, wherein the test is at least one of provided to the patient before the patient uses the external medical device, provided to the patient before the patient receives the external medical device, provided to the patient on a periodic basis during the patient's use of the external medical device, and provided to the patient dynamically in response to patient interaction with the external medical device.

Clause 81. The external medical device of any of clauses 63-80, wherein the test comprises at least one of an inductive reasoning test, an intelligence quotient test, a situation judgment test, a working memory test, a psychomotor ability test, a language test, a technology ability test, a color blindness test, a hearing test, a vision test, a steadiness test, and a movement test.

Clause 82. The external medical device of any of clauses 63-81, wherein the controller is configured to determine the ability of the patient relating to the operation of the medical device based on the response and configure the device to match the ability of the patient to a patient interaction mode of the device.

Clause 83. The external medical device of any of clauses 63-82, wherein the controller is configured to determine the patient interaction mode of the medical device from a plurality of patient interaction modes.

Clause 84. The external medical device of any of clauses 63-83, wherein the plurality of patient interaction modes comprise at least a first patient interaction mode, a second patient interaction mode, and a custom patient interaction mode, wherein the first patient interaction mode is associated with patients having a different ability relating to the operation of the medical device than the second patient interaction mode.

Clause 85. The external medical device of any of clauses 63-84, wherein the controller is configured to match the ability of the patient to a custom patient interaction mode, and wherein, in the custom patient interaction mode, the controller is configured to adjust or customize one or more features or functions of the external medical device based on the determined mode.

Clause 86. The external medical device of any of clauses 63-85, wherein the controller is configured to adjust or customize at least one of the following based on the determined mode: an audio output volume of the medical device, an audio output tonal frequency of the medical device, an output display color of the medical device, an image or font display size of the medical device, a display contrast of the medical device, a type of response requested by the output of the medical device, and a type of alarm, alert, or instruction issued by the medical device.

Clause 87. The external medical device of any of clauses 63-86, wherein the controller is configured to determine at least one of the following: a respiration rate of the patient, a heart sound and movement of the patient, a lung sound and movement of the patient, a tissue fluid level of the patient, a blood pressure of the patient, a glucose level of the patient, and a blood oxygenation level of the patient.

Clause 88. The external medical device of any of clauses 63-87 comprising at least one of a cardiac monitor, a defibrillator, and a wearable defibrillator.

Clause 89. The external medical device of any of clauses 63-88 comprising a wearable external medical device.

Clause 90. The external medical device of any of clauses 63-89, wherein the wearable external medical device comprises a garment worn by the patient.

Clause 91. The external medical device of any of clauses 63-90, wherein the wearable external medical device comprises adhesive patches including at least one of sensing electrodes and therapy electrodes.

Clause 92. An external medical device comprising: monitoring circuitry configured to monitor a cardiac condition of a patient using the external medical device; and a controller configured to: receive at least one patient input and a second input; determine a patient interaction mode of the external medical device based on the at least one of the patient input and the second input; and adapt the patient interaction mode of the external medical device over time based on the at least one of the patient input and the second input.

Clause 93. The external device of clause 92, wherein the second input is a non-patient user input.

Clause 94. The external device of clause 92 or 93, wherein the second input is a condition input.

Clause 95. The external device of any of clauses 92-94, wherein the condition input is an external condition input.

Clause 96. The external device of any of clauses 92-95, wherein the condition input is a medical condition input.

Clause 97. A monitoring system for monitoring a condition of an ambulatory patient, the system comprising: an external medical device comprising: a device housing; at least one response button extending from the housing; and at least one pressure sensor associated with the at least one response button for measuring a pinch force exerted against the button by the patient; and a controller in communication with the external medical device, the controller being configured to: receive and process information from the at least one pressure sensor; determine a pinch force of the patient based on the received and processed information; compare the pinch force to one or more previous pinch force measurements of the patient; and provide information about results of the comparison to the patient and/or to a caregiver.

Clause 98. The system of clause 97, wherein the external medical device comprises a first response button positioned on a first side of the device and a second response button positioned on a second side of the device, the response buttons being positioned to be pinched between one or more of a thumb and an index finger of the patient, a pad of the thumb and pads of the index finger and the middle finger of the patient, and the pad of the thumb and a medial-lateral surface of the index finger of the patient.

Clause 99. The system of clause 97 or 98, wherein the provided information about the results of the comparison comprises an indication when pinch force changes beyond a threshold amount and/or an indication when pinch force changes from a baseline pinch force by more than a predetermined percentage.

Clause 100. The system of any of any of clauses 97 to 99, wherein the information about results of the comparison comprises a determination of a change in a condition of the patient.

Clause 101. The system of clause 100, wherein the change in the condition of the patient comprises a clinically significant change.

Clause 102. The system of clause 100 or 101, wherein the patient condition comprises one or more of an overall health of the patient, a progression of cardiovascular disease of the patient, and a prediction of a likelihood that the patient will experience a cardiac event.

Clause 103. The system of any of clauses 97-102, wherein the one or more previous pinch force measurements are received from a database of previous pinch force measurements stored on computer readable memory associated with the controller.

Clause 104. The system of any of clauses 97-103, further comprising a wireless transceiver configured to wirelessly transmit the determined patient condition from the controller to an external source.

Clause 105. The system of any of clauses 97-104, further comprising an audio or visual output device configured to provide a notification to the patient regarding the results of the comparison.

Clause 106. The system of clause 105, wherein the notification comprises an instruction to seek help or to contact a physician or caregiver.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

FIG. 5 is an example screen for presenting an output or test on an external medical device;

FIG. 6 is an example screen for presenting an output or test on an external medical device;

FIG. 7 is an example screen for presenting an output or test on an external medical device;

DETAILED DESCRIPTION

Figure 1:
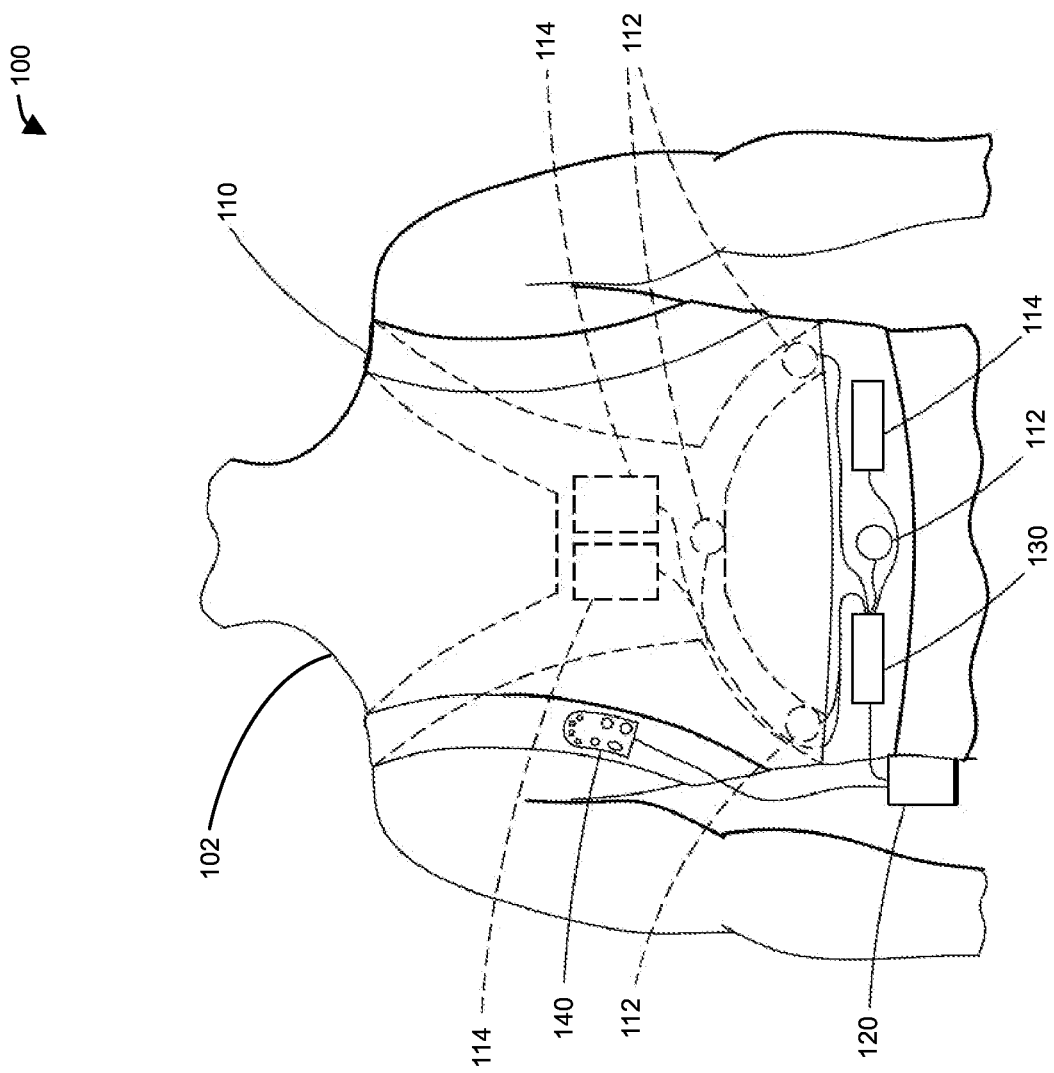
FIG. 1 is an example schematic drawing of a wearable medical device.

As used herein, the singular form of "a", "an", and "the" include plural referents unless the context clearly dictates otherwise. For the purposes of this specification, unless otherwise indicated, all numbers expressing quantities of ingredients, reaction conditions, dimensions, physical characteristics, and so forth used in the specification and claims are to be understood as being modified in all instances by the term "about."

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

Aspects of the present disclosure are directed to monitoring and/or therapeutic medical devices that allow a determination of one or more abilities of a patient. In some implementations, the devices may be configured to determine an interaction mode or otherwise set patient interaction features (e.g., patient interaction settings, functions, parameters, and/or values) for the device based on the determined patient abilities. For example, such abilities may include any of the patient's physical, mental, psychomotor, visual, hearing abilities, memory retention, skills and/or other such characteristics of the patient. In some implementations, the abilities as assessed by the device in accordance with this disclosure may relate to one or more operational features and functions of the underlying device. For instance, the device may evaluate a patient's abilities in determining whether and to what degree a patient is able to respond to instructions provided by the device.

In various examples, patient abilities as described herein may be assessed via an automated process administered by a medical device, medical evaluations and/or observations by a medical caregiver and/or representative, or provided as input by the patient, as described in further detail below. By enabling an interaction mode and/or adaptively changing patient interaction features (e.g., settings and functions of the device determined with respect to an individual patient), the patient's use of and experience with the medical device may be improved.

For example, interaction modes involve setting such interaction features as device display and touch screen settings (e.g., font size, color, display layouts, display pattern, style, brightness, contrast, video settings, sensitivity to patient input, etc.), informational settings (e.g., amount and complexity of detail presented to the patient, language, amount and complexity of textual, image, animation, and/or video information, etc.), readability settings, gesture recognition settings, device use pattern settings, voice recognition settings, Braille input settings, patient interaction security settings, and device alarm and alert configurations (e.g., volume, type of alert, tone, frequency of occurrence of alerts, sequence of alerts, and audible and spoken alert settings), etc.

In one scenario, a prescriber (e.g., a caregiver or other designee) or patient service representative (PSR) or other person involved in deploying the medical device can have the ability to set up the device depending on whether the patient is a technology savvy patient or a technology naïve patient. In an implementation, the PSR can preset a graphical interface on the device based on his/her observation or evaluation/test of the patient's ability and/or skill level in performing a series of tasks and actions relating to the medical device. The appropriate patient interaction mode and/or baseline patient interaction features may be selected based on one or more of the above. The patient can be reevaluated at random or specified intervals, for example on a periodic basis (e.g., based on device triggered reminders or during follow-up patient visits to a health care facility) and the appropriate interaction mode can be adjusted (e.g., dynamically and/or in real-time, or after a preconfigured delay) based on the results of the reevaluation. In some examples, the patient can select or request certain configurations in one or more preconfigured modes, such as the font size of visual displays. In some examples, such configurations may be adjusted from their baseline or default values and/or settings by the patient during use of the device. In some examples, the device may be configured to automatically adapt such configurations and/or settings in accordance with input received from the patient and/or observations of patient use of the device. In some examples, the device may be configured to allow for adjustment to a readability level of the messages. For example, the device may automatically adapt to adjust the readability level of the messages based on observations of the patient's input and interactions with the device. For instance, the device may increase or decrease an amount of text presented in a particular message, or otherwise increase or decrease the complexity of the information in the message. In some cases, to make messages easier to interpret, the device may add graphics, images, or animations to the message in one readability level, while there may be fewer or no graphics, images or animations to a message in another readability level.

In some examples, the medical device can comprise communications circuitry for receiving updated or new patient interaction modes from an external source. New patient interaction modes and device settings can be received automatically, such as by batch download when updated modules are available. If the selected modules are not stored locally on the external medical device, the selected interaction mode can be downloaded from a remote source. Patient interaction modes can also be selected for and provided to the patient by a non-patient user, for example a patient service representative or other medical caregiver. In some examples, during or following a test, the patient can initiate communication with the service representative to discuss the selected mode and/or to suggest or request changes to the device settings based. For example, an audio and/or video communication link between the patient and representative can comprise a real-time telephone call, a real-time video call (e.g., a Skype® call, a FaceTime® call, or other video conferencing call), a Push-to-Talk (PTT) connection, or other communication link capable of communicating audio and/or video data between the patient and the service representative.

In some implementations, a medical device can be configured to dynamically and/or adaptively adjust one or more patient interaction features of the medical device in response to patient, environmental and/or contextual conditions. For example, dynamically adjusting patient interaction features can include adjusting the patient interaction features in substantially real-time with corresponding changes in the underlying patient, environmental and/or contextual conditions. For example, the interaction features may be adjusted after a delay from when a change in underlying one or more patient, environmental and/or contextual conditions occur. In implementations, such a delay may be a predetermined value and/or user-configurable delay value provided through an interface.

For example, a medical device may be configured to adjust one or more patient interaction features based on a condition input, such as a predetermined relationship with one or more sensed input signals from one or more patient, environmental, and/or contextual sensors associated with the medical device. For example, such adjustments may be made dynamically and automatically in response to changing conditions. For instance, the adjustments may occur within an open or closed loop system control scheme. Further, such adjustments may be made adaptively in response to learning patterns in the underlying changing conditions.

A condition input derived from a predetermined relationship between the patient interaction features and sensed input signals as described above may be based on any known or learned relationship between the underlying parameters, including single or multi-variable linear, non-linear (such as quadratic, logarithmic, exponential, etc.), and other kinds of relationships. In some cases, the predetermined relationship may be based on binary classifications, transformations of the underlying signals (e.g., discrete forms, frequency and/or other domains, etc.), and/or statistical analysis. In some examples, the relationship may be based on performing a multivariate regression analysis of the sensed input signals and deriving one or more equations to describe the relationship.

Additionally, one or more techniques may be employed to match, verify, and/or correlate information from one or more types of sensors against other types of sensors. For instance, if a patient is performing a physical activity such as running or jogging, heart rate sensor information may be correlated with accelerometer information to confirm the activity and the intensity of the activity in determining one or more patient interaction features.

The medical device may also be configured to analyze a plurality of input signals in order to adaptively effect changes to one or more underlying patient interaction features. For instance, the medical device may effect changes to the patient interaction features based on a series of decision nodes. Each node may be based on logic implemented to test one or more sensed input signals (individually or in a predetermined combined format) from one or more sensors of the medical device against a threshold. An output of such decision nodes may be to increase, decrease, or otherwise adjust one or more patient interaction features of the medical device.

In some implementations, machine learning classification or regression tools may be trained and validated on training/validation populations of sensed values corresponding to signals from the one or more sensors. Such machine learning based systems can be implemented in accordance with the principles described herein such that the medical device can adaptively adjust its patient interaction features in accordance with changing patient, environmental, and/or contextual conditions. Any of the above techniques can be used alone or in combination in order to establish a relationship between the patient interaction features of the medical device and the sensed signals.

According to another aspect of the disclosure, a medical device can be configured to monitor and provide information representative of changes in a patient's hand strength, grip strength, or pinch strength. In some instances, monitoring pinch strength includes instructing the patient to perform different dexterity tests and comparing test results to standard or baseline values. Information about changes in hand, grip, and/or pinch strength can be provided to the patient's physician for review. Measures of hand strength are used in physical therapy as indicators of overall health and, in particular, cardiac health. In a similar manner, it is believed that hand strength can be an important independent surrogate parameter to assess the outcome and risk of morbidity and mortality. For example, a decrease in grip strength has also been found to correlate with an increase in death overall, an increase in both cardiovascular and non-cardiovascular mortality, an increase in the risk of myocardial infarction, and an increase in the risk of stroke. Research suggests that "low grip strength is associated with increased susceptibility to cardiovascular death in people who do develop cardiovascular disease." A similar pattern has been observed for non-cardiovascular diseases suggesting that "low muscle strength might not play a major causal part in the occurrence of cancer, falls, fractures, or the need for hospital admission for respiratory illness, but that, as with incident cardiovascular disease, low muscle strength predisposes to a fatal outcome if these non-cardiovascular diseases develop." See Leong et al., *Prognostic value of grip strength: findings from the Prospective Urban Rural Epidemiology (PURE) study*, Lancet 2015, 386:266-273 (Jul. 18, 2015), which is incorporated by reference in its entirety (hereinafter "the *Lancet* study").

More specifically, in the Lancet study, the researchers determined that each 5 kg (about 11 lbs.) decrease in grip strength over the course of the study was linked to a 16% higher risk of dying from any cause, a 17% higher risk of dying from heart disease, a 9% higher risk of stroke, and a 7% higher risk of heart attack. The connections between grip strength and death or cardiovascular disease remained strong, even after the researchers adjusted for other things that can contribute to heart disease or death, such as age, smoking, exercise, and other factors. It is noted that grip strength was determined to be a better predictor of death or cardiovascular disease than blood pressure. In some instances, the medical device can be configured to measure the patient's pinch strength by, for example, instructing the patient to press and hold the device response buttons. In that case, in such implementations, pinch strength is correlated with hand and grip strength and used, for example, as an indicator of patient condition and/or as a predictor of mortality and cardiac mortality.

Example External Medical Devices

This disclosure relates to components, modules, subsystems, circuitry and/or techniques for use in medical devices configured to monitor a patient and/or provide treatment to the patient based on one or more detected health conditions. For example, a medical device can include a plurality of sensing electrodes that are disposed at various locations of the patient's body and configured to sense or monitor cardiac signals (e.g., ECG signals, heart sounds, etc.) and/or other physiological parameters as described in further detail below. For example, such devices may be mobile cardiac telemetry (MCT) and/or continuous event monitoring (CEM) devices.

In some implementations, medical devices as described herein can be configured to monitor a patient for cardiac arrhythmia conditions such as bradycardia, ventricular tachycardia (VT) or ventricular fibrillation (VF). Other medical conditions may include, e.g., atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventrical arrhythmias such as premature ventricular contractions (PVCs) and accelerated idioventricular rhythm. In the case of treatment devices, such as, pacing and/or defibrillating devices, if an arrhythmia condition is detected, the device can automatically provide a pacing or defibrillation pulse or shock to treat the condition.

Example Therapeutic Wearable Medical Device

With reference to FIG. 1, an example of an external medical device 100, such as a wearable defibrillator, for use with the systems and methods as described herein, is shown. Non-limiting examples of wearable defibrillators are disclosed in U.S. Pat. Nos. 4,928,690; 5,078,134; 5,741,306; 5,944,669; 6,065,154; 6,253,099; 6,280,461; 6,681,003; 8,271,082; and 8,369,944; the disclosures of each of which are incorporated herein by reference in their entireties. The external medical device 100 comprises a plurality of sensing electrodes 112 that can be disposed at various positions about the patient's body. The sensing electrodes 112 are electrically coupled to a medical device controller 120 through a connection pod 130. In some examples, some of the components of the external medical device 100 are affixed to a garment 110 that can be worn on the patient's torso. For example, as shown in FIG. 1, the controller 120 can be mounted on a belt worn by the patient. The sensing electrodes 112 and connection pod 130 can be assembled or integrated into the garment 110 as shown. The sensing electrodes 112 are configured to monitor the cardiac function of the patient (e.g., by monitoring one or more cardiac signals of the patient). While FIG. 1 shows four sensing electrodes 112, additional sensing electrodes can be provided, and the plurality of sensing electrodes 112 can be disposed at various locations about the patient's body.

The external medical device 100 can optionally comprise a plurality of therapy electrodes 114 that are electrically coupled to the medical device controller 120 through the connection pod 130. The therapy electrodes 114 are configured to deliver one or more therapeutic defibrillating shocks, pacing pulses, and/or TENS pulses to the body of the patient if it is determined that such treatment is desired. The connection pod 130 can comprise electronic circuitry and one or more sensors that are configured to monitor patient activity, contextual information, and/or environmental information. For example, such sensors can include a motion sensor, accelerometer, gyroscopes, GPS sensors, indoor positioning devices, humidity sensors, pressure sensors, moisture sensors, temperature sensors, etc. In some examples, the external medical device 100 can be a monitoring only device that omits the therapy delivery capabilities and associated components (e.g., the therapy electrodes 114).

As shown in FIG. 1, the external medical device 100, which can be a wearable medical detector can comprise a patient interface pod 140 that is electrically coupled to, integrated in, and/or integrated with, the interface of the medical device controller 120. In another implementation, the patient interface pod 140 can be configured to communicate wirelessly with the controller 120, for example, using a Bluetooth®, Wireless USB, ZigBee, Wireless Ethernet, GSM, or other type of communication interface. The patient interface pod 140 typically includes a number of buttons or a touch screen by which the patient, or a non-patient user may communicate with the controller 120, and a speaker and/or a display by which the controller 120 may communicate with the patient or the non-patient user. For example, if the controller 120 determines that the subject is experiencing a cardiac arrhythmia, the controller 120 may issue an audible alarm via a loudspeaker (not shown) on the controller 120 and/or the patient interface pod 140 alerting the patient and any bystanders to the subject's medical condition. The controller 120 may also instruct the patient to press and hold one or more buttons on the controller 120 or on the patient interface pod 140 to indicate that the patient is conscious, thereby instructing the controller 120 to withhold the delivery of one or more therapeutic defibrillating shocks. If the patient does not respond, the device may presume that the subject is unconscious, and proceed with the treatment sequence, culminating in the delivery of one or more defibrillating shocks to the body of the patient. In some embodiments, functionality of the patient interface pod 140 may be integrated into the controller 120.

In some implementations, a computing device, such as, a smartphone or tablet computer, can be used in place of the patient interface pod 140. The smartphone or tablet computer can be wirelessly coupled to the interface of the medical device controller 120, e.g., using a Bluetooth®, Wireless USB, ZigBee, Wireless Ethernet, GSM, or other type of communication interface, and perform the functions of the patient interface pod 140.

Figure 2B:
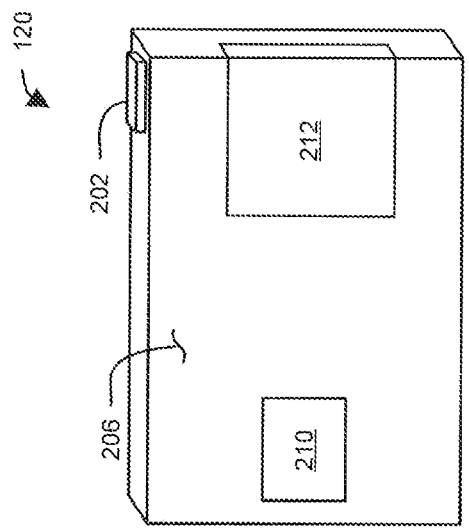
FIG. 2B is a schematic drawing of a rear view of the example controller of FIG. 2A.
Figure 2A:
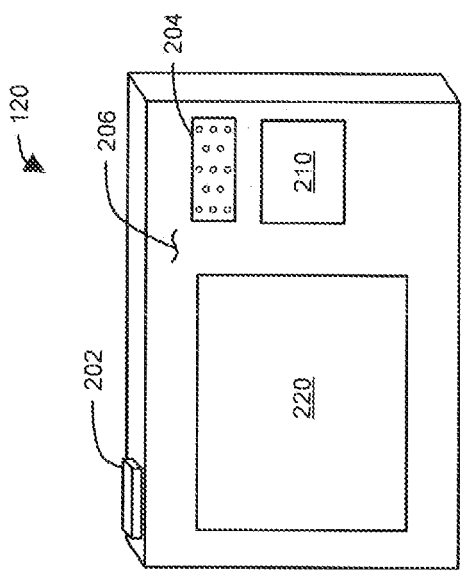
FIG. 2A is a schematic drawing of a front view of an example controller for a wearable medical device.

With reference to FIGS. 2A-2B, an example of the medical device controller 120 is illustrated. The controller 120 can be powered by a rechargeable battery 212. The rechargeable battery 212 can be removable from a housing 206 of the medical device controller 120 to enable a patient and/or caregiver to swap a depleted (or near depleted) battery 212 for a charged battery. The controller 120 comprises an interface such as a touch screen 220 that can provide information to the patient, caregiver, and/or bystanders. For example, the touch screen 220 can be used as described herein in determining abilities of the patient, put in a predetermined patient interface mode, and/or have one of more of the touch screen 220 features adapted in accordance with the patient's abilities. The patient and/or caregiver can interact with the touch screen 220 to control the external medical device 100. The controller 120 also comprises a speaker 204 for communicating information to the patient, caregiver, and/or the bystander. The controller 120 comprises one or more response buttons 210. In some examples, when the controller 120 determines that the patient is experiencing cardiac arrhythmia, the speaker 204 can issue an audible alarm to alert the patient and bystanders to the patient's medical condition. In some examples, the controller 120 can instruct the patient to press and hold one or both of the response buttons 210 to indicate that the patient is conscious, thereby instructing the medical device controller 120 to withhold the delivery of therapeutic defibrillating shocks. If the patient does not respond to an instruction from the controller 120, the external medical device 100 can determine that the patient is unconscious and proceed with the treatment sequence, culminating in the delivery of one or more defibrillating shocks to the body of the patient. The medical device controller 120 can comprise one or more port(s) 202 to removeably connect sensing devices (e.g., ECG sensing electrodes 112) and/or therapeutic devices (e.g., therapy electrodes 114 shown in FIG. 1) to the medical device controller 120.

In some examples, alarms that are issued by the medical devices are described herein can include auditory alarms, such as melodies, verbal alarms, and other types of audible alarms. For example, alarms as described herein include those that are described in international standard IEC 60601-1-8 titled "Medical electrical equipment—Part 1-8: General requirements for basic safety and essential performance—Collateral standard: General requirements, tests and guidance for alarm systems in medical electrical equipment and medical electrical systems."

Figure 11:
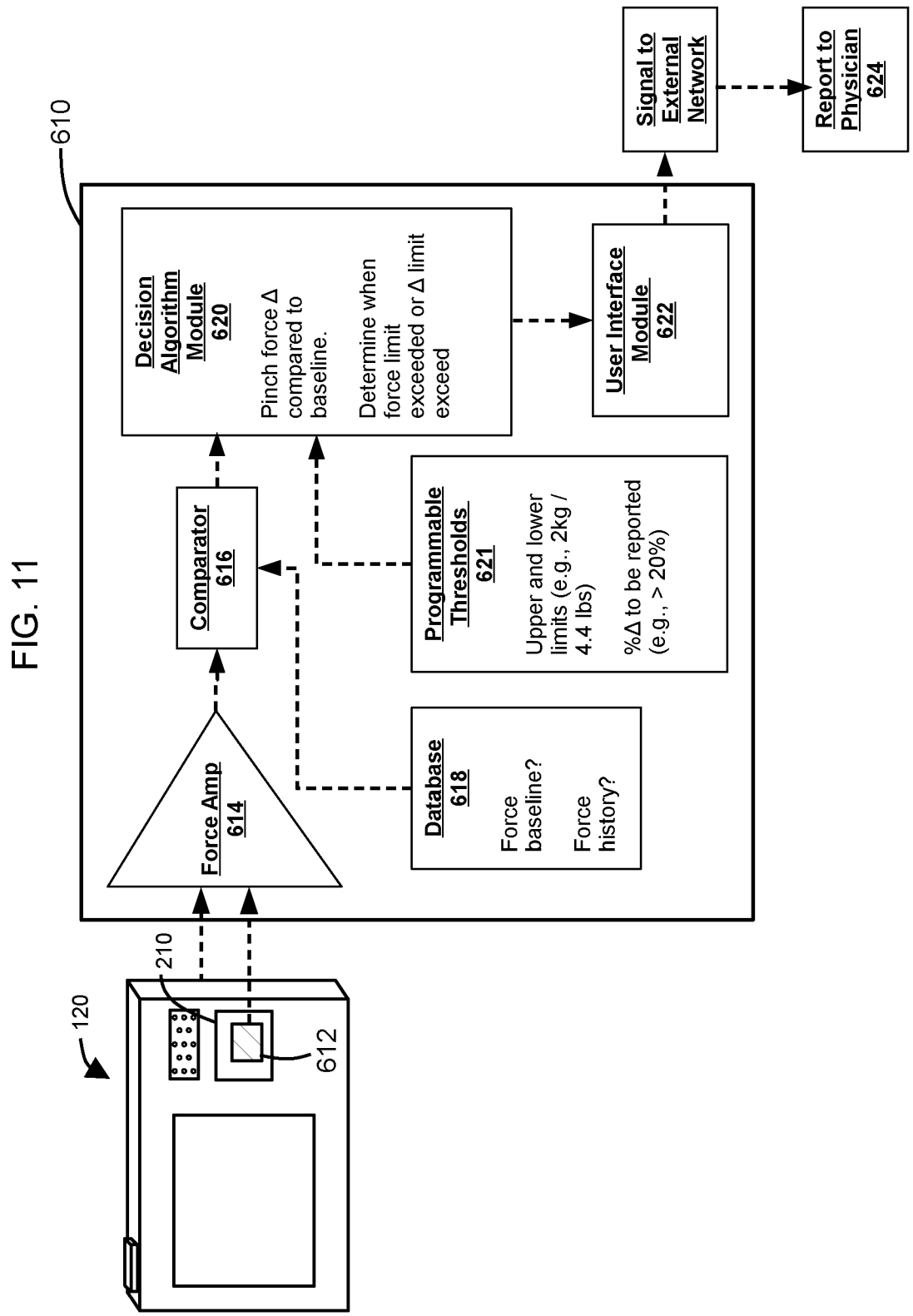
FIG. 11 is a schematic drawing of a system for measuring pinch strength of a patient including a controller for a medical device in accordance with an aspect of the disclosure.

In some examples, the response buttons 210 can comprise one or more force or pressure sensors for measuring a pinch strength of the patient while manipulating the response buttons 210. As discussed hereinabove, typical pinch strength measurements for a 2-finger pinch generally range between about 9 lbs. to 16 lbs., and vary based on age, gender, and other physical characteristics. The pressure sensors can be embedded on each response button 210 and configured to measure a force exerted against the button 210 by the patient's fingers and/or thumb. For example, the patient may place his/her thumb on the response button 210 on the front side of the controller 120 and place his/her index finger on the response button 210 on the rear side of the controller 210. When prompted by the controller 120, the patient may move his/her fingers together in a pinching motion, thereby depressing the buttons 210. The controller 120 can be configured to determine a force exerted against the depressed buttons 210 based on measurements from the respective force or pressure sensors. For example, as shown in FIG. 11, in some examples, the pressure sensors can be associated with electronic circuitry for deriving a force measurement from signals measured by the pressure sensors, comparing pinch strength to previously measured results, and drawing conclusions about patient condition based on the comparison.

Figure 3:
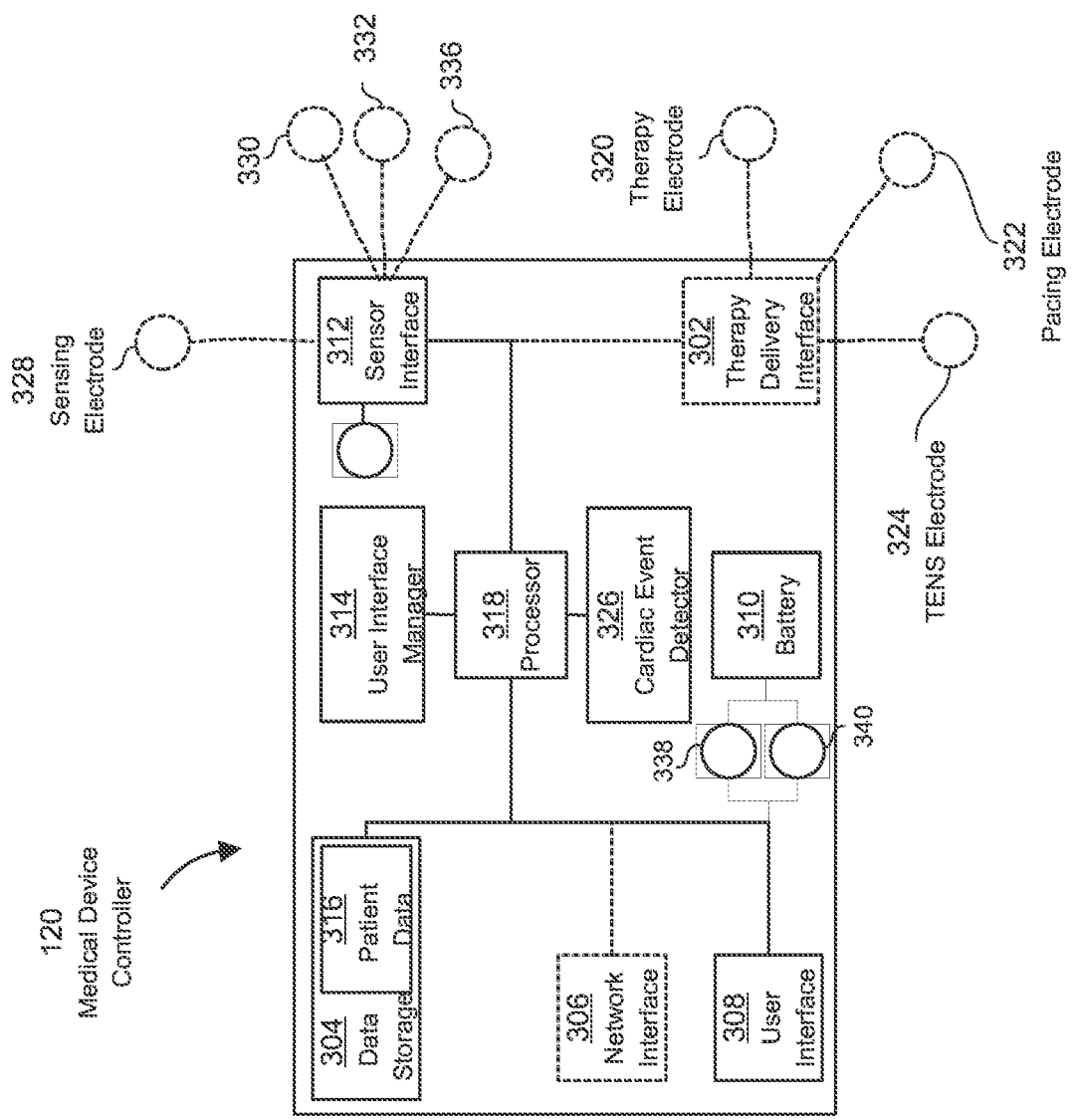
FIG. 3 is an example block diagram illustrating functional components of a controller for a wearable medical device.

With reference to FIG. 3, a schematic example of the medical device controller 120 of FIGS. 1, 2A, and 2B is illustrated. As shown in FIG. 3, the controller 120 comprises at least one processor 318, an interface manager 314, a sensor interface 312, an optional therapy delivery interface 302, data storage 304 (which can comprise patient data storage 316), an optional network interface 306, an interface 308 (e.g., including the touch screen 220 shown in FIGS. 2A and 2B), and a battery 310. The sensor interface 312 can be coupled to any one or combination of sensors to receive information indicative of cardiac activity. For example, the sensor interface 312 can be coupled to one or more sensing devices including, for example, sensing electrodes 328, contact sensors 330, pressure sensors 332, and accelerometers or motion sensors 334. The therapy delivery interface 302 (if included) can be coupled to one or more electrodes that provide therapy to the patient including, for example, one or more therapy electrodes 320, pacing electrodes 322, and/or TENS electrodes 324. The sensor interface 312 and the therapy delivery interface 302 can implement a variety of coupling and communication techniques for facilitating the exchange of data between the sensors and/or therapy delivery devices and the controller 120.

In some examples, the network interface 306 can facilitate the communication of information between the controller 120 and one or more other devices or entities over a communications network. For example, the network interface 306 may be configured to communicate with a server (e.g., a remote server) where a caregiver can access information related to the patient. As discussed in more detail below with reference to FIG. 4, the network interface 306 can facilitate communication between the medical device controller 120 and a base station associated (e.g., paired) with the medical device controller 120.

In some examples, the medical device controller comprises a cardiac event detector 326 to monitor the cardiac activity of the patient and identify cardiac events experienced by the patient based on received cardiac signals. In other examples, cardiac event detection can be performed using algorithms for analyzing patient ECG signals obtained from the sensing electrodes 328. Additionally, the cardiac event detector 326 can access patient templates (e.g., which can be stored in the data storage 304 as patient data storage 316) that can assist the cardiac event detector 326 in identifying cardiac events experienced by the particular patient (e.g., by performing template matching algorithms).

The at least one processor 318 can perform a series of instructions that control the operation of the other components of the controller 120. In some examples, the interface manager 314 is implemented as a software component that is stored in the data storage 304 and executed by the at least one processor 318 to control, for example, the interface component 308. The interface manager 314 can control various output components and/or devices of the medical device controller 120 to communicate with external entities consist with various acts and/or display screens described herein. For example, such output components and/or devices can comprise speakers, tactile and/or vibration output elements, visual indicators, monitors, displays, LCD screens, LEDs, Braille output elements, and the like.

Example Base Station for an External Medical Device

Figure 4:
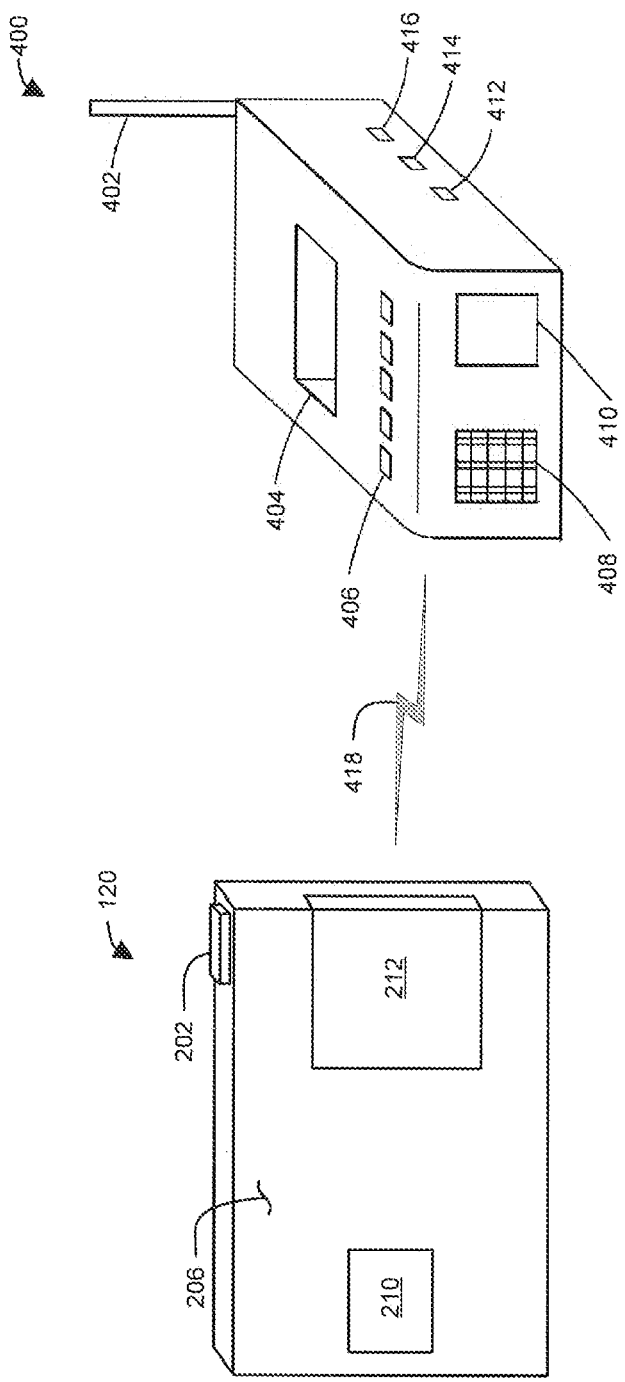
FIG. 4 is a schematic drawing of an example medical monitoring device in wireless communication with a base unit.

With reference to FIG. 4, in some examples, the medical device controller 120 can be in communication via wired or wireless communication link 418 with a base station 400 capable of performing a number of different functions. As illustrated, the base station 400 comprises an antenna 402, a battery charging bay 404 capable of charging a rechargeable battery for the medical device controller 120, one or more buttons 406, a speaker 408, a display 410, and one or more communication interfaces 412, 414, and 416, such as, a device communication interface 412 to receive information from the controller 120, a telephone network interface 414 to communicate, via a telephone network, the information received from the medical device controller 120, and a network interface 416 to communicate, via a wired network connection, the information received from the medical device controller 120. The medical device controller 120 can provide, for example, information regarding the patient's medical condition and/or the status of the medical device to the base station 400, and the base station 400 can store and/or communicate information received from the medical device controller 120 over the wired or wireless communication network to a remote location.

Evaluation of Patient Function, Ability, and/or Skill

The external medical device, or another computing device, such as a desktop computer or a tablet computer, can provide an output that requests a response for testing and/or determining an ability of a patient. As described in more detail below, the ability of the patient can be used to determine a patient interaction mode of the external medical device and/or to provide a report or analysis of the patient's ability. In some implementations, the ability of the patient can be used to determine a baseline set of patient interaction features which can then be adaptively adjusted over time as further input is received. The output can comprise one or more requests for response from the patient or a non-patient user (e.g., a PSR, medical caregiver and/or representative, etc.). For example, the output can comprise a test or exercise including a plurality of prompts (e.g., questions) that request patient responses and/or actions. In some examples, the output can be displayed as part of the interface of the controller 120 on, for example, the touch screen 220 (shown in FIGS. 2A, 2B, and 4) or another visual display of the external medical device 100, for example, as a combination of text, drawings, visual indicators, animation, and/or embedded videos. The output can be controlled, for example, by the interface manager 314 (shown in FIG. 3) of the controller 120. In another example, the output can be provided as audio output via speaker 204 (FIG. 2A) of the controller 120, for example voice instructions, alarms, or audible alerts. In some examples, the output can be a tactile output, such as a continuous vibration, a pulsed vibration, or a mixed vibration. In an example in which another computing device, such as a desktop computer or tablet computer, provides the output, the computing device can receive responses to the output and communicate the responses and/or an analysis or report of the responses to the controller 120 of the external medical device 100.

The controller 120 can be configured to determine or receive a response from the patient or a medical caregiver and/or representative to the output via the interface of the controller 120, such as the touch screen 220, response buttons 210, and the microphone, and/or via one or more of the sensors of the sensor interface 312, such as the contact sensors 330, pressure sensors 332, accelerometers or motion sensors 334.

In an example, the output requests a response from the patient. For example, as shown in FIG. 5, the controller 120 can play a series of sounds at increasing tonal frequencies (e.g., pitch), volumes, and/or durations and request the patient to press a "yes" button displayed on the touch screen 220 or make a movement to indicate when the patient can hear the sound. Based on this test, for example, the controller 120 can automatically determine a patient interaction mode (or set of initial patient interaction features) in which audible alerts and voice commands are provided at the tonal frequencies, volumes, and durations that the patient has indicated that he/she can hear. The controller 120 can add a vibration element to more critical alarms or commands to ensure that a patient with more limited hearing capacities is notified of more critical alarms, such as a treatment alarm issued before providing a treatment shock.

In another example, the output can request a response from the third party, such as a caregiver or a patient service representative (PSR) or other person involved in assigning, configuring, and/or deploying the external medical device to the patient. For example, as shown in FIG. 6, the controller 120 can provide the PSR or prescriber with a brief questionnaire on the touch screen 220 to fill out indicating a patient's response to various questions, for example, questions directed to assessing the patient's cognitive ability. The PSR or prescriber can read the questions to the patient and input the patient's answers via the touch screen 220, or have the patient read the questions and input the answers via the touch screen 220. The PSR or prescriber can be provided with another screen, for example, as shown in FIG. 7, via which he/she can rate or rank other abilities of the patient, such as, the patient's reading ability, hearing ability, fine motor skills, dexterity, and mental/emotional status based on the PSR or prescriber's observation of the patient's behavior. In some implementations, the controller 120 can recommend a patient interaction mode or initial patient interaction features to the PSR based on the responses, but allow the PSR to override the recommendation or independently set the patient interaction mode or features. In some implementations, the controller 120 can automatically adapt the device to a predetermined set of baseline settings and/or values for patient interaction with the device, and automatically adjust the settings and/or values over time based on observations of and/or input from the patient.

In some implementations, rather than or in addition to prompting a PSR or other third party, the device may receive input directly from the patient. For instance, the controller 120 can automatically determine the ability of the patient based on the patient's responses to the questions described in FIGS. 6 and 7. As such, the patient may be able to enter his/her responses to such questions and/or prompts, and the device can automatically set the patient interaction mode based on the patient's responses.

In some implementations, the controller 120 can recommend a patient interaction mode to the patient based on the responses, but allow the patient to override the recommendation or independently set the patient interaction mode. For instance, the controller's 120 recommendation can be based on analysis of historical data relating to patient interaction observations. For instance, the historical data can include information relating to a plurality of patients' response times to a plurality of device alerts and alarms, durations and intensities of such alerts and alarms, individual patient display settings and preferences, and preferences relating to levels of informational detail presented by the devices. For example, such analysis of historical data can be based on any of machine learning, multivariate analysis, statistical techniques, or the like. In another example, the PSR, prescriber, or patient can be provided an ability to skip device-administered testing and select an appropriate patient interaction mode of the external medical device for the patient or otherwise assess the patient and/or configure the device based on his/her own observation of the patient.

In an example, a response time of the patient's response to the output or test and/or a pattern of the patient's response to the output or test can be used to determine an ability of the patient. The determined ability can then be used in setting baseline patient interaction settings and/or a patient interaction mode of the external medical device 100. For example, a response time (or a lack of response) that transgresses a response time threshold for an output can be used to determine, for example, that the patient cannot hear an audible alarm or does not understand (or cannot see) instructions provided via text on the touch screen 220. A pattern of a patient repeatedly responding incorrectly to a prompt or instructions can be used to determine, for example, that the patient does not understand the instructions. A patient's response within a response threshold and/or repeated correct response to a prompt can indicate that the patient has a sufficient ability to operate the device in a current patient interaction mode. In another example, the controller 120 can determine the patient interaction mode to set one or more thresholds for responding to an alarm or instructions based on the patient's response to the output or test and/or a pattern of the patient's response to the output. For example, the patient interaction mode of an external medical device 100 of a patient that typically responds to an alarm, but that also typically takes too long to respond to the alarm, can be set manually or automatically to allow increased time periods for responding to alarms.

In some examples, the output or tests can comprise instructions and/or requests directed to both: i) the PSR, the prescriber, or the caregiver; and ii) the patient. For example, output including a first series of instructions directed to a caregiver can request the caregiver to demonstrate to the patient how to assemble the garment of a wearable external medical device 100, and output including a second series of instructions directed to patient can request the patient to assemble the garment based on what they have learned from caregiver's demonstration. In an implementation, the caregiver can input an indication of the patient's ability to correctly assemble the garment via the interface of the controller 120 based on his/her observation of the patient, e.g., by providing a ranking or score, or answering one or more questions about the patient's attempt to assemble the garment. In another example, referring again to FIGS. 6 and 7, the PSR can have the patient input the his/her answers to the questions via the touch screen 220, and the PSR can input his/her observations to a patient evaluation form provided by the controller 120 after observing the patient answer the questions.

The output or tests can comprise a plurality of different questions or requests directed to the patient and/or a non-patient user, such as the PSR or the caregiver. In some examples, the external medical device can determine a subsequent question or request to be provided to a patient based on a patient's response to a prior question or request, for example, as discussed below with respect to FIG. 8. In another example, if a patient response to a question is incorrect, a next question presented to the patient can be selected to be a relatively easier or a simpler question, or vice-versa. If a patient fails to respond to audible prompt from the external medical device, the external medical device can follow the audible prompt with a visual prompt or tactile prompt, or vice-versa.

In some implementations, the device can be configured to monitor a use of the device in determining appropriate patient interaction mode or features. For example, the device can be configured to monitor the patient's use of the medical device during device operation (e.g., monitoring and/or treatment of the patient by the external medical device). For example, the device can include sensors configured to identify certain events, conditions, or device use patterns that can damage the device, possibly injure the patient, or otherwise indicate that the patient is incorrectly using the device, and/or that reduce the device's ability to monitor and, in some cases, provide therapy to the patient. For example, the sensed information can identify that the patient attempts to operate the device in an incorrect manner, that the patient is failing to respond to prompts or alarms from the device in a timely manner, that the patient is having trouble taking care of the device (e.g., forgetting to replace or recharge device batteries in a timely manner), and/or that the patient is misusing the device (e.g., dropping or damaging the device). In another scenario, the device may include an external condition input, for example from a humidity sensor that may detect an event indicating that the device is in an environment having higher than a predetermined permitted humidity level (e.g., the device is taken into the shower by the patient when it should not). In another scenario, the external condition input can include a signal indicating a proximity to a location, such as, a proximity to the Bluetooth® signal of a car, and the device can determine an appropriate patient interaction mode or features for the patient when operating the car. For example, a patient car interaction mode may limit the number of prompts and/or alerts issued to the patient so as to avoid distracting the patient during driving and/provide a simpler interface for responding to prompts and/or alerts. In some scenarios, the external condition input can include an indication of a level of light at a location at which the device is located, and the device can adjust a brightness of the display to an appropriate brightness for the level of light. In one scenario, the external condition input can include an input from a motion sensor, which can indicate that the device has experienced an impact, and the device can implement a simpler patient interaction mode or features in response to the impact so that a patient that has fallen or dropped the device can more easily operate the device.

In another scenario, the device may include a medical condition input, for example, from the cardiac event detector 326 that may detect a cardiac event, such as, that the patient is experiencing an arrhythmia, and the device can implement a simpler patient interaction mode or features during the arrhythmia event so that a patient in duress can more easily operate the device.

In another example, the device can monitor an actual device operation during monitoring of the patient, e.g., a treatment alarm issued before providing a treatment shock, wherein if the patient does not respond to the treatment alarm (e.g., by holding down one or more response buttons 210), the device can deliver the treatment shock to restore normal heart rhythm. The controller 120 can determine and use the patient's response (and timing thereof) to the treatment alarm (or a pattern of responses to multiple treatment alarms) to determine an ability of the patient interaction mode of the external medical device. For example, the controller 120 can automatically adjust such patient interaction settings from their baseline values, such as increase the volume or add a vibration to the treatment alarm if a pattern of patient responses indicate that the patient is responding outside a threshold period of time to respond and/or barely responding within the threshold, e.g., due to the patient not initially recognizing the alarm or understanding what to do in response.

The output or tests from the controller 120 can be provided to the patient before the patient receives or uses the external medical device 100, before the medical device begins monitoring the patient, on a periodic basis during the patient's use of the external medical device 100, and/or dynamically in response to patient interaction with the external medical device 100 during the patient's use of the external medical device 100.

In an example, an initial output or test is provided to the patient during an initial setup of the external medical device 100, for example, when the PSR or prescriber first assigns the external medical device 100 to a patient, and can be configured to include follow-up output or tests after the initial setup during monitoring of the patient by the external medical device 100. For example, the external medical device 100 can determine an initial patient interaction mode or baseline patient interaction settings for the device based on the output or tests provided during the initial setup, and adapt the patient interaction mode and/or settings over time with further information. For example, the adapting may occur immediately after the initial test results are received and processed, at a predetermined later time, or over time based on periodic follow-up tests or real time input and/or observations of the patient.

In another example, the output or tests can be provided in response to a request from the PSR or prescriber, or can be automatically provided by the device upon assignment or configuration of the external medical device 100 to a patient for the first time. In an example, the controller can require one or more mandatory tests to be completed by the patient or the PSR before the PSR or prescriber can fully deploy the device with the patient. In another example, the controller 120 can be configured to automatically administer a test to the patient on a particular date or in response to a particular patient operation of the device such that the patient can self-administer the test. For example, if the patient is continually failing to respond to a particular alert, the controller 120 can provide an output or test to the patient directed to determining the patient's ability to hear a sound associated with the alert, see text or images associated with the alert, or cognitively understand an action requested by the device in response to the alert. In some examples, the PSR or prescriber can remotely deploy a test for a patient to complete in the patient's home or elsewhere, e.g., by instructing the controller 120 of the external medical device 100 via the Internet and/or other networks to prompt the patient to complete the test. For example, if the PSR or physician suspects that the patient's cognitive ability is declining, e.g., due to Alzheimer's disease or some other form of dementia, the PSR can instruct the device to re-test the patient and/or update the patient interaction mode of the device based on the patient's updated cognitive ability, for example, by implementing a simpler patient interaction mode or reducing a number of features available to the patient in the current patient interaction mode when the patient's cognitive ability is determined to have declined.

Figure 8:
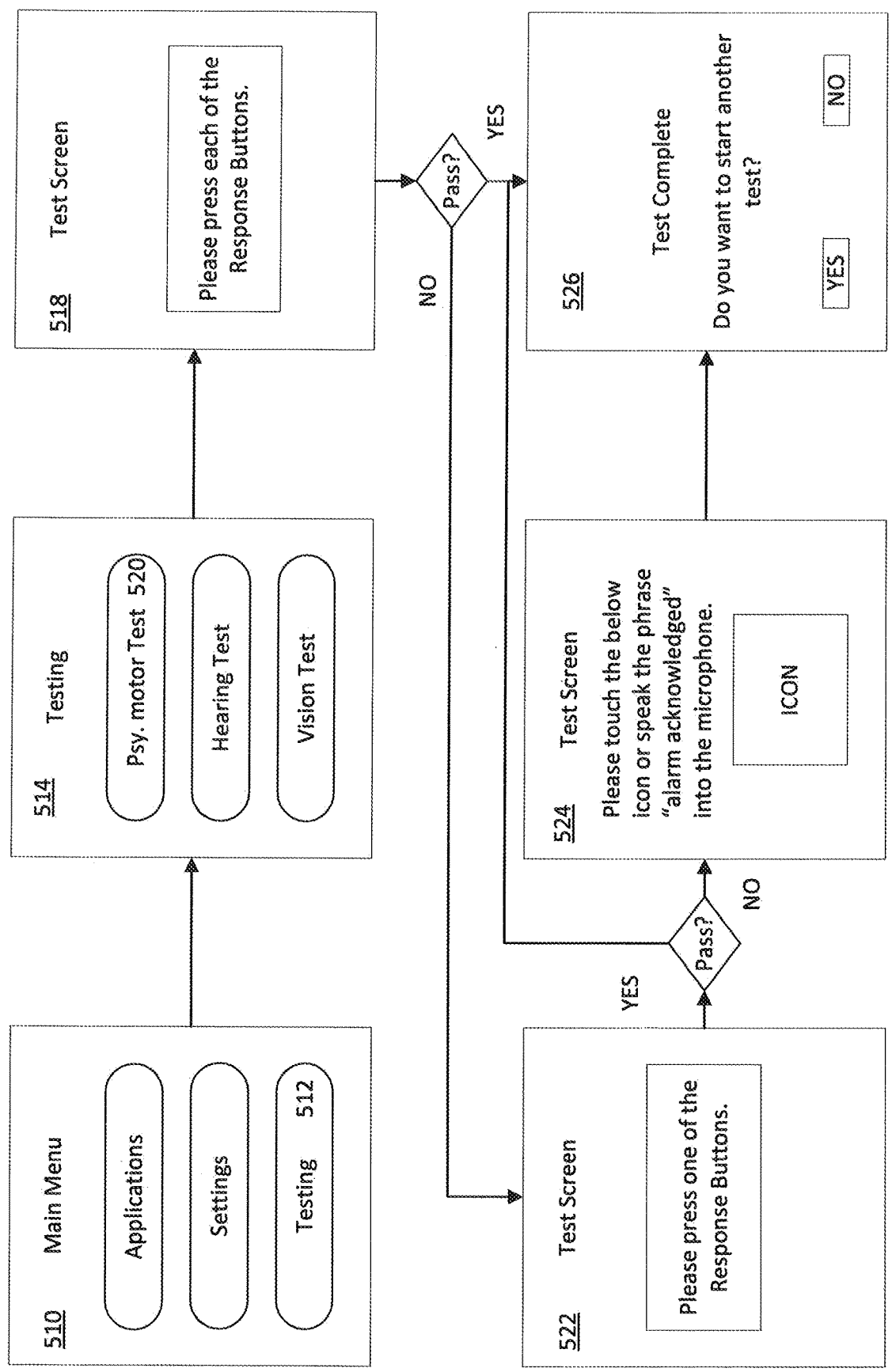
FIG. 8 is an example set of screens for presenting an output or test on an external medical device.

With reference to FIG. 8, an example set of screens that can be displayed to the patient and the non-patient user, such as a PSR or prescriber on, for example, the touch screen 220 (shown in FIGS. 2A, 2B, and 4) or another visual display are illustrated. The interface of the controller 120 enables a PSR or prescriber to perform numerous activities related to selecting a test to be provided to the patient, and the patient to perform numerous activities related to completing the selected test. The PSR or prescriber can be provided with a main menu or home screen 510 including a menu of options or functions that the device can perform. One of the options, as shown by button 512, can be an option to access "Testing". Selection of the button 512 causes the interface to provide the patient or non-patient user with an interactive list 514 of available testing modules. Alternatively or in addition, the external medical device 100 can comprise a dedicated testing module button located on the device housing. Pressing the testing module button can cause the screen to advance to the interactive list 514. After reviewing some or all of the available testing module options, the non-patient user (e.g., the PSR or prescriber) selects a specific testing module to access. For example, in the case of a touch screen display, the patient or non-patient user can simply touch the portion of the screen, such as button 512, corresponding to the testing module of interest. In other examples, the patient or non-patient user can toggle through available options using arrows, buttons, keys, or other data entry features of the external medical device 100 to record a selection. In other examples, a selection can be entered audibly, by speaking a portion of the name of the testing module of interest. In that case, a microphone associated with the device can record the patient or non-patient user's command and audio processing techniques can be used to record the correct selection.

The PSR or prescriber can give the controller 120 to the patient to complete the selected test. The test is presented as one or more questions or requests to the patient, and can be displayed to the patient on a single screen or over the display of multiple different screens.

For example, as shown in example test screen 518, the patient can be prompted via text on the screen and/or a via voice command to press each of the response buttons 210. During device monitoring of the patient, pressing each of the response buttons 210 can be requested in response to a treatment alarm issued before providing a treatment shock in order to avoid shocking the patient in an unnecessary scenario. Accordingly, it can be desirous to test the patient's ability to operate the response buttons 210 of the controller and/or respond to a treatment alarm. If the patient successfully presses each of the response buttons 210 within a threshold period of time during the test, the screen can advance directly to the test complete screen 526. The controller 120 can select a patient interaction mode of the external medical device 100 for the patient that requires each of the response buttons 210 to be pressed when a response from the patient is requested based on the patient's successful operation of each of the response buttons 210. However, if the patient does not press each of the response buttons 210 within the threshold period of time, the test can advance to test screen 522, which prompts the patient to press one of the response buttons 210. If the patient successfully presses the one response buttons 210 within a threshold period of time, the screen can advance directly to the test complete screen 526. The controller 120 can select a patient interaction mode of the external medical device 100 for the patient that requires only one of the response buttons 210 to be pressed when a response from the patient is requested. However, if the patient does not press the one response button 210 within the threshold period of time, the test can advance to test screen 522, which can provide an alarm or alert to the PSR or prescriber that the patient appears incapable of actuating the response buttons 210 and/or prompts the patient to attempt another form of responding to a prompt from the controller 120, such as touching an element displayed on the touch screen 220 of the interface.

At the completion of a particular testing module, as shown by module completed screen 526, a non-patient user (e.g., the PSR or prescriber) can be provided with a screen informing him or her that the selected testing module has been completed. The module completed screen 526 can, for example, inform the patient or the non-patient user that the specific module is complete and can inquire whether the patient or the non-patient user wishes to review any part of the testing module. Alternatively or in addition, the module completed screen 526 can identify or suggest another related module that the PSR or prescriber can have the patient complete to provide additional information about an ability of the patient either in general or in relation to operation of the medical device. For example, the module completed screen 526 for a testing module testing a patient's vision or sight, can ask the PSR or prescriber whether he or she wants the patient to take a further test to test the patient's hearing ability.

Further, it is appreciated that the screens and screen sequences described herein are for illustration only and should not be construed as being the only way to implement the concepts described herein. For example, in the context of presenting a test to a patient, the sequence of screens or the screens themselves can be changed from those shown in FIGS. 5-8 to include other screen sequences or screens related to patient testing without departing from the spirit of the concepts described herein.

Assess General Ability

The controller 120 is configured to determine an ability of the patient based on the input and responses received from the patient and/or the third party. The controller 120 can generate data that represents the ability of the patient based on the input or responses received form the patient and/or the third party. The controller 120 can generate or accumulate reports prepared based on the data, and provide the reports to interested parties, such as the PSR, the patient's family, caregivers, and/or a responsible or prescribing physician. The reports can indicate a rating or level assigned to an ability of the patient, such as a technology comfort level, a reading level, etc., or an indication of a determined patient characteristic, such as color blindness, memory loss, hearing loss at specific frequencies or volumes, etc. For example, the output or tests can be configured to assess one or more of the following: an inductive reasoning ability of the patient, an intelligence quotient of the patient, a situation judgment ability of the patient, a working memory ability of the patient, a psychomotor ability of the patient, a language ability of the patient, a hearing ability of the patient, a vision ability of the patient, and a level of steadiness of a hand of the patient, a technology comfort level of the patient, and the like. The output or tests can comprise one or more of the following: an inductive reasoning test, an intelligence quotient test, a situation judgment test, a working memory test, a psychomotor ability test, a language test, a technology ability test, a color blindness test, a hearing test, a vision test, a steadiness test, a movement test, and the like.

In an example, the report can further provide an indication of an ability of the patient relating to one or more specific operations of the external medical device 100. For example, the report can indicate device operations and/or functions that the patient can and cannot perform, such as a capability to press the response buttons 210, hear certain audible alarms at specific frequencies, view text at certain font sizes on the touch screen display 220, etc., and/or associate one or more of the determined skill levels with one or more of the device operations and/or functions.

Assess for Mode

In another example, the controller 120 is configured to determine a patient interaction mode of the external medical device 100 based on the input and responses received from a patient and/or a non-patient user. For example, the controller 120 can determine an ability of the patient relating to the operation of the medical device based on the input or responses and configure the device to match the ability of the patient to a patient interaction mode of the device. The interface manager 314 is configured to cause the external medical device 100 to enter the determined patient interaction mode. As described above, the controller 120 receives input or responses to output or tests provided to the patient and/or the non-patient user. The responses can comprise input representing at least one of the following: a) a patient input and b) a non-patient user input including an observation and/or evaluation of the patient (e.g., a PSR's observation of the patient, a medical representative or caregiver's evaluation of the patient, etc.) and the controller 120 can determine a patient interaction mode based on the one or more inputs.

The controller 120 can determine the patient interaction mode of the external medical device 100 from a plurality of patient interaction modes. The plurality of patient interaction modes can have different features and/or functions as described in more detail below. In another example, the controller 120 is configured to adjust or customize one or more features or functions of a custom patient interaction mode of the external medical device 100 based on patient input or responses.

Technology Comfort

In an example, the controller 120 can determine the patient interaction mode based on a technology comfort level of the patient as determined from patient input. For example, the determined patient interaction mode can be selected from a plurality (two or more) of patient interaction modes, each patient interaction mode having at least one different operational characteristic. For example, the determined patient interaction mode can be selected from a) a first technology comfort mode, b) a second technology comfort mode, and c) a custom technology comfort mode. The first technology comfort mode is characterized by having predominantly more textual elements on an interface of the external medical device 100 than the second technology comfort mode. The second technology comfort mode is characterized by having predominantly more image, animation, or video-based elements on an interface of the external medical device 100 than the first technology comfort mode, e.g., the second technology mode is designed for a less sophisticated technology patient or a patient with a lower level of cognition or response ability. The custom technology comfort mode is configured by adjusting or customizing one or more features or functions of the external medical device 100 based on patient input.

When the external medical device 100 enters one of the first technology comfort mode, the second technology comfort mode, the custom technology mode, and any other patient interaction mode, the external medical device 100 sets or changes one or more of the following features or functions of the external medical device 100: a) output features or functions of the external medical device 100, b) visual output features or functions of the external medical device 100, c) audio output features or functions of the external medical device 100, and/or d) tactile output features or functions of the external medical device 100.

The output features or functions of the external medical device 100 comprise at least one of the following: a) an order or a sequence of one or more alarms, alerts, or instructions issued by the external medical device 100, b) a type of the one or more alarms, alerts, or instructions issued by the external medical device 100, b) a frequency of occurrence of one or more alarms, alerts, or instructions issued by the external medical device 100, c) an escalation pattern of the one or more alarms, alerts, or instructions issued by the external medical device 100, and/or d) a response requested by the one or more alarms, alerts, or instructions issued by the external medical device 100.

The visual output features of functions of the external medical device 100 comprise at least one of the following: a) selection of one or more visual elements for an interface of the external medical device 100, b) an arrangement of the visual elements on the interface, b) an output display color of the one or more visual elements, c) an image or font display size of the one or more visual elements, and/or d) a display contrast of one or more visual elements or the interface.

The audio output features of the external medical device 100 comprise at least one of the following: a) selection of one or more audio output elements including one or more of a tone alarm or alert, a gong alarm or alert, a siren alarm or alert, or verbal messages, b) an order or sequence of the one or more audio elements provided by the external medical device 100, c) an audio output volume of the one or more audio output elements, d) a tonal frequency (e.g., pitch) of the one or more audio output elements, and/or e) an escalation pattern of the one or more audio output elements.

The tactile output features of the medical device comprise at least one of the following: a) selection of one or more tactile mechanisms including one or more of a continuous vibration, a pulsed vibration, or a mixed vibration, b) an order or sequence of the one or more tactile mechanisms provided by the external medical device 100, c) an intensity of the one or more tactile mechanisms, d) a frequency of vibration of the one or more tactile mechanisms, and/or e) an escalation pattern of the one or more tactile mechanisms.

Figure 9:
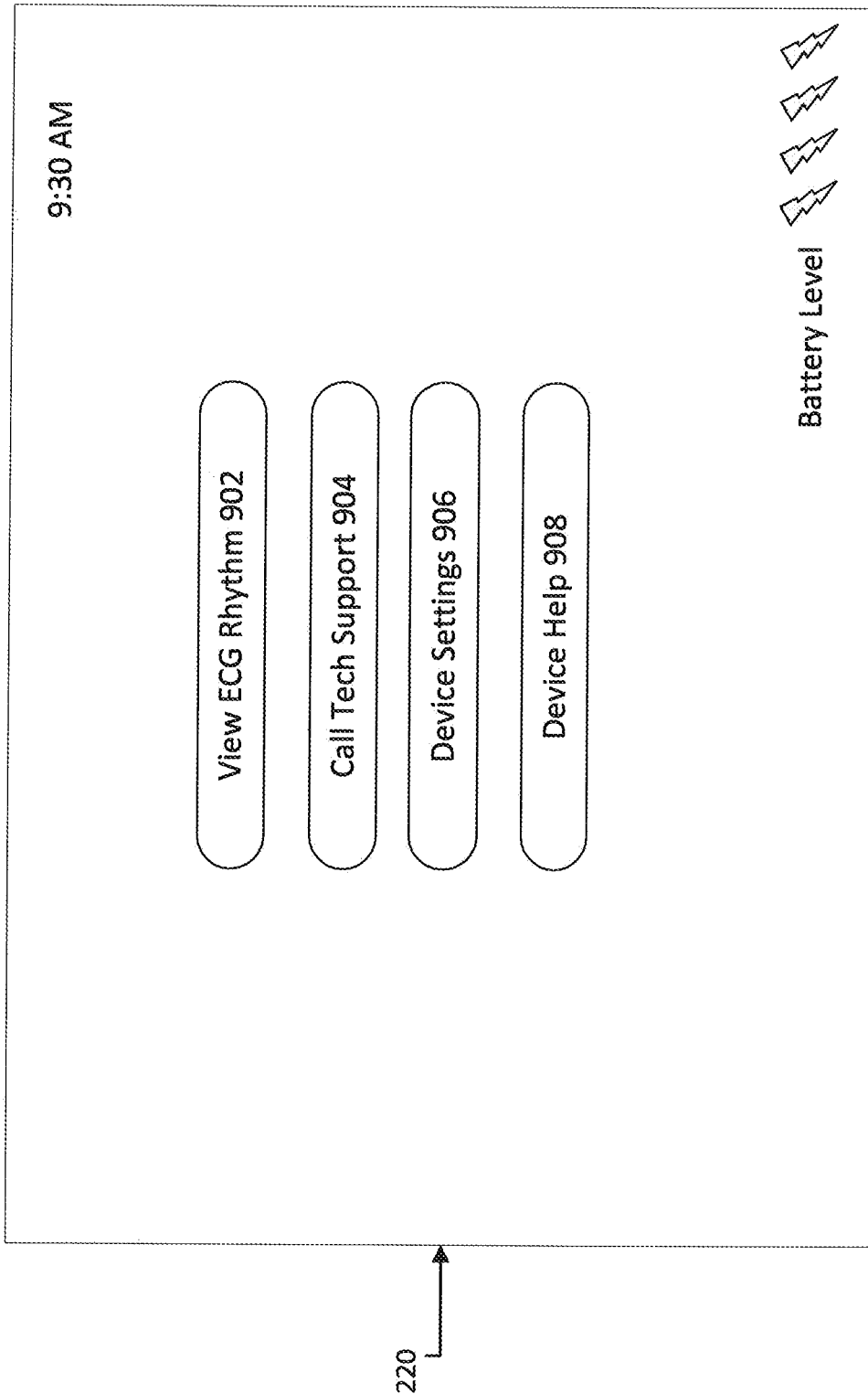
FIG. 9 is an example screen for presenting a patient interaction mode of an external medical device.

Referring to FIG. 9, in an example, the first technology comfort mode can provide an interface that enables the patient, e.g., via menu buttons 902-908, to view his/her ECG rhythm in real time, receive error codes, e.g., for troubleshooting with technical support, receive an indication of specific electrodes that have fallen off the patient, textual based help screens for addressing patient issues with the device, and access device settings, such as a display brightness of the touch screen 220, a volume of voice instructions associated with a help screen, and the like. In another example, the first technology comfort mode can provide an interface that enables the patient to initiate one or more device tests, such as a walk test or a health survey, change language settings, change sleep settings, and view training demos.

Figure 10:
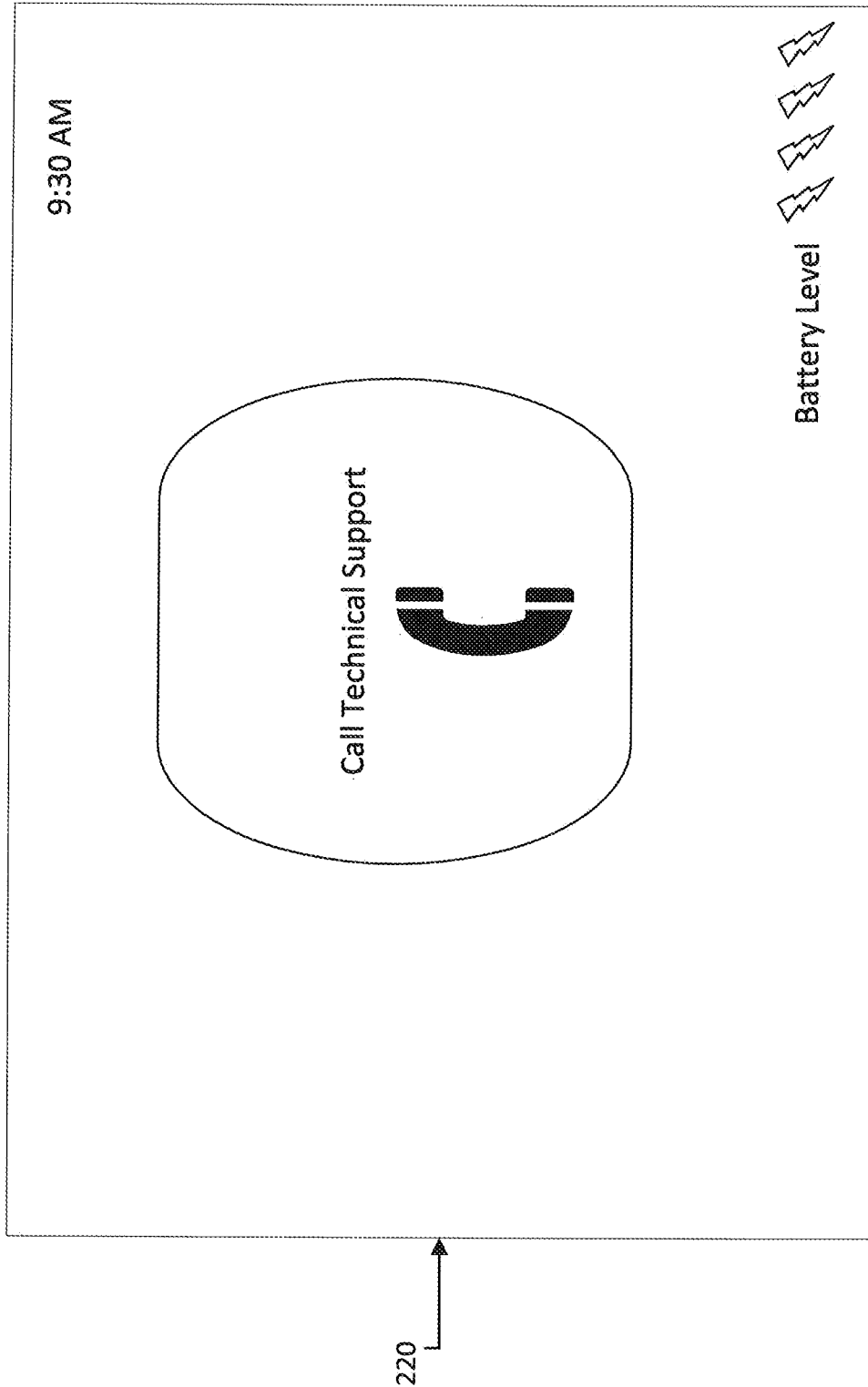
FIG. 10 is an example screen for presenting a patient interaction mode of an external medical device.

In contrast, the second technology comfort mode can turn off the touch screen 220 display completely and provide the patient with only critical audible and/or tactile alerts, such as, a treatment alarm before providing a treatment shock, to which the patient can respond by pressing the response buttons 210. In another example, as shown in FIG. 10, the second technology comfort mode can provide a basic visual patient interface via the touch screen 220, such as a battery level indication and single patient selectable element to call technical support.

In another example, the controller 120 can determine a custom patient interaction mode similar to the first technology comfort mode for an elderly patient (e.g., over age 65) with relatively weak eye sight, mild hearing loss, and a mild level of Alzheimer's. For example, the custom patient interaction mode can provide an interface with large font, high contrast, clearly defined shapes, and voice guidance that is spoken slowly and loudly. Device alarms and communications can be kept to a minimum. For example, controller 120 can require the patient to call technical support rather than attempt to take any actions on their own.

Language

The output or tests can be configured to determine a language ability of the patient with respect to a selected interface language of the external medical device 100, e.g., English, Spanish, etc., and the controller 120 can select an interface language for the device text and voice commands based on the patient's input to the test. For example, the output or test can comprise typical device voice commands or alarms played back in the selected language and ask the patient to make a selection on the touch-screen 220 based on the playback. In another example, the output or test can be configured to determine a patient's understanding of basic device screens, utterances, commands, instructions, etc., to determine a language listening, reading, and comprehension ability of the patient. For example, a command "press response buttons" or "tap the screen" can be voiced, and if the patient response is correctly recorded, the device can proceed to the next aspect of the test, or the patient can be asked to read a passage or listen to a voice instruction and answer one or more questions about the content of the passage or voice instruction. In another example, to assess or determine a patient's reading ability, a test can be displayed on the screen and with instructions to "press response buttons" for a period of time, e.g., 5 seconds, and the patient response recorded to assess or determine the reading ability of the patient. In still another example, a patient's ability to follow instructions can be tested by providing a series of screens instructing the patient to perform a portion of a walk test. The controller 120 can determine a patient interaction mode with less text and/or voice commands and more pictorial elements displayed on the touch screen 220 for patients that are determined to have lower language listening, reading, and comprehension ability. For example, as shown in FIG. 10, a call support button can additionally comprise a graphic icon of a "telephone" to indicate to the patient that pressing the button will place a call.

Hearing

The output or tests can be configured to determine a hearing ability of the patient. In an example, the speaker 204 (FIG. 2A) of the external medical device 100 or a speaker of the desktop computer or the tablet computer can output a sound sample at a given frequency and the patient is asked a "yes" or "no" question on whether he/she heard the sound. Each time the patient answers "yes", the next sample will be played, at a higher frequency. When the patient answers that they cannot hear a played sound, the test ends and the device can determine based on the responses from the patient the frequencies at which the patient can hear sounds from the device. Alternatively, the controller 120 can replace the "yes" or "no" test with a three answer test (I can hear/I can barely hear/I cannot hear) to more accurately detect when hearing difficulty begins. The controller 120 can determine a patient interaction mode for the external medical device 100 in which alerts and other audible output is emitted only at frequencies at which the patient has indicated that they can hear sounds. For example, the controller 120 can have a baseline frequency profile for each audible messages or alert, and the controller 120 can use the results of the hearing test to adjust (using Fast Fourier Transforms or other methods) the audible messages or alerts to remove or reduce the presence of hard to hear frequencies and/or increase the presence of easier to hear frequencies. A similar adjustment or determination of the patient interaction mode can be made for the volume of sounds, the duration of sounds, e.g., alarm durations, and/or a threshold time given to the patient to response to an alarm or prompt.

In another example, the speaker 204 (FIG. 2A) of the external medical device 100 can play sounds for the patient at random intervals. The PSR or the device can instruct the patient to touch the screen or press response button(s) 210 when he/she hears a sound. The patient can indicate whether the sound was a strong sound or faint sound. If the patient stops responding, the device (or PSR) can assume that the end of the patient's hearing range has been reached, which can produce more accurate results regarding the patient's range of hearing because the likelihood of some patients confirming that they can hear a sound when they actually do not is reduced.

In another example, if patient performs poorly on the hearing test, e.g., by indicating hearing loss early in the hearing test, the system can adjust a tactile alarm functionality so that tactile alarms are present more often or for all audible messages. For example, in a patient interaction mode there can be no tactile alarm/notification when the battery is low. If the patient performs poorly on the hearing test, the controller 120 can enable the tactile notification in the patient interaction mode or switch to another patient interaction mode that enables tactile notification to ensure that the patient is notified of the alarm/notification.

Psychomotor

The output or tests can be configured to determine a psychomotor ability of the patient, e.g., a relationship between the cognitive functions of the patient and the patient's physical movement. In an example, the controller 120 can output instructions to the patient to press both response buttons 210 of the external medical device 100 simultaneously, for example, as described above with respect to FIG. 8. In another example, the controller 120 can cause the touch screen 220 to display a line with instructions to the patient to follow the line on the screen with his/her finger. The controller 120 can determine the patient's ability to correctly follow the line via the touch screen 220. The controller 120 can enable easier mechanisms or alternative mechanisms of response for patients that have more limited psychomotor ability. For example, if the patient has trouble selecting or interacting with touch screen elements, the controller 120 can determine a patient interaction mode in which more or all of the patient input or responses can be received via the response buttons 210. In another example, if the patient does not have the psychomotor ability to use either the response buttons 210 or the touch screen 220, the controller 120 can determine a patient interaction mode in which patient input is received via the microphone and processed with voice recognition software. For example, the patient can speak into the microphone a predetermined phrase, such as "Stop alarm" (e.g., to indicate acknowledgement of an alarm) or "Don't shock", in response to a treatment alarm before providing a treatment shock so that he/she is not unnecessarily shocked. In another example, the patient can speak into the microphone a phrase, such as "call technical support", to instruct the controller 120 to place a call to technical support.

Hand Tremor

The output or tests can be configured to determine whether the patient has a hand tremor. In an example, the controller 120 can request the patient to press down on the touch screen 220 portion of the patient interface and record the patient's contact pattern over a period of time, e.g., 10-30 seconds. The sensor interface 312 of the external medical device 100 can detect shifting/changes above a threshold as measured by the interface, and based on the detected shifting/changes determine a degree to which the patient's hand is affected by a tremor. The controller 120 can determine a patient interaction mode in which features or functions of the device that require more steady hand movements, such as interaction with the touch screen 220 are reduced or removed entirely. For example, the controller 120 can determine a patient interaction mode that requests input via the response buttons 210 (or via voice response as described above) to alarms or notifications if the controller 120 determines that the patient has a significant hand tremor.

In another example, as described above, the controller 120 can request the patient to draw a pattern on the touch screen 220 portion of the interface or follow a line on the touch screen. In another example, the external medical device 100 can receive input including a PSR or prescriber's observation of the patient performing one or more tasks, such as drinking from a glass, holding arms outstretched, writing, and drawing a spiral.

Vision

The output or tests can be configured to determine a vision or sight ability of the patient. The controller 120 can prompt the patient to indicate whether he/she can make out shapes and/or text font in the display of the interface. The controller 120 can determine a patient interaction mode having larger text font or less text font and more icons for patients that are determined to have limited vision ability. In another example, the controller 120 can directly prompt the patient an optimum or preferred text font size, color, and/or icon shape to customize the features and functions of the patient interaction mode to the patient.

Color Blindness

The output or tests can be configured to determine whether a patient is color blind and a type of color blindness of the patient. In one example, the controller 120 can assume that the patient knows that they are color blind and what kind of color blindness they suffer from. During patient setup, the controller 120 can prompt the patient to answer a question indicating whether they are color blind and what type of color blind. In another example, the controller 120 can display via the touch screen 220 a Red/Green and Blue/Color blindness tests including a picture that is composed of various shades of red/green with numbers hidden inside and requests the patient to respond by indicating which number is inside each circle. An ability of the patient to detect the correct number over several samples enables the controller 120 to determine if the patient is color blind, and if so, the type of color blind.

In an example, the controller 120 can determine a patient interaction mode for the device that sets display colors of the touch screen 220 to be only those colors that the patient can see and differentiate between. In another example, if a color blindness mode is enabled, the controller 120 can replace solid colors indicating caution/warning/notification with patterned/hashed versions of the colors further differentiate colors or call attention the colors. In other examples, if color blindness mode is enabled, the controller 120 can present/overlay standardized alarm symbols on the touch-screen with an appropriate color to further indicate to the patient that a specific screen or icon on the screen has a specific meaning.

Other Tests

The output or tests can be configured to determine whether a patient has Alzheimer's disease or another condition that can cause confused thinking, trouble focusing or memory problems, and depression. The controller 120 can select a more simple interface, e.g., the second technology comfort mode discussed above, for a patient that has Alzheimer's or another disease that limit's the patient's ability to operate or understand features or functions the external medical device 100.

Adaptive Mode Assessment

In some examples, the controller 120 is configured to adapt the patient interaction mode over time based on the input and responses received from the patient and/or a non-patient user (e.g., a PSR or caregiver). For example, as described above, the controller 120 can determine a patient interaction mode in an initial period, e.g., when the device is first assigned to the patient, and adapt the patient interaction mode of the external medical device 100 over time based on the input and response received from the patient and/or third party subsequent to setting the initial mode. The controller 120 can be configured to monitor a pattern of patient interactions with the external medical device 100 over the period time or over a number of patient interactions with the external medical device 100 and adapt the patient interaction mode of the external medical device 100 over time by changing the patient interaction mode from a first one of a plurality of patient interaction modes to a second one of the plurality of patient interaction modes based on the monitored pattern of patient interactions. For example, the first patient interaction mode can be associated with a patient having a different ability relating to an operation of the medical device than the second patient interaction mode.

In some implementations, the controller 120 is configured to initiate based on a baseline or initial or baseline set of patient interaction features. The controller 120 can then be configured to adapt such patient interaction features over time based on the input and responses received from the patient and/or the non-patient user (e.g. PSR or caregiver). For example, as described above, the controller 120 can determine the initial patient interaction features in an initial period, e.g., when the device is first assigned to the patient, and adapt the patient interaction features of the external medical device 100 over time based on the input and response received from the patient and/or non-patient user subsequent to the initial period. The controller 120 can be configured to monitor a pattern of patient interactions with the external medical device 100 over the period time or over a number of patient interactions with the external medical device 100 and adapt the patient interaction features of the external medical device 100 over time by changing and/or adjusting the patient interaction features based on the monitored pattern of patient interactions. For example, if the patient is having trouble responding to a certain type of alarm (e.g., a gong alert), the device can be configured to switch the alarm type to a different alarm type (e.g., verbal instructions) to ensure that the patient has perceived the alarm.

In another example, the controller 120 is configured to determine the patient interaction mode as a custom patient interaction mode, and in the custom patient interaction mode, the controller 120 is configured to adjust or customize one or more features or functions of the custom patient interaction mode of the external medical device 100 based on the patient input. For example, the controller 120 can adjust or customize at least one of the following features or functions of the external medical device 100: a) output features or functions of the external medical device 100, b) visual output features or functions of the external medical device 100, c) audio output features or functions of the external medical device 100, and d) tactile output features or functions of the external medical device 100.

In an example, during operation of the external medical device 100, e.g., after deployment and during live monitoring of the patient by the device, the controller 120 can analyze patient-device interaction trends over a period of time or over a number of previous interactions and adapt the patient interaction mode or interaction features of the device based on the monitored interactions. For example, the controller 120 can track an amount of time it takes a patient to respond to a specific alarm (or to all device alarms in general) to learn an average or typical patient response time to the specific alarm (or all alarms in general). The controller 120 can adapt the interface to output different types of alarms/alerts if the patient response time is poor (e.g., slower than desired). In an example, if a patient continually fails to respond to a battery change notification, the controller 120 can increase the urgency of the notification by increasing the volume of the notification or adding a tactile aspect to the notification, as a vibration. For example, the controller 120 can monitor whether the patient responds to the alert in an appropriate manner, for example, in the case of a device having a replaceable battery, a correct response can be to remove the exhausted or nearly exhausted battery and replace it with a fully charged battery. In other examples, the patient can respond to a low battery warning by connecting the device and/or controller to a power source for charging. For example, for a previous battery change alarm (or over a time period of the last 2 weeks), if the average patient response time before the battery is changed is about 1 hour, which is longer than may be desired, the controller can adapt the battery change notification or alarm to be more frequent (persistent) or louder, or the controller 120 can output a voice command instructing the patient to replace the battery within 30 minutes.

In some examples, prior to changing a patient interaction mode of the device or changing a feature or function within a patient interaction mode of the device, the controller 120 can provide a prompt to the patient. For example, the prompt can indicate that the mode is going to be changed and provide some information about the change, and in some examples, request the patient's authorization to make the change.

The controller 120 can learn patient response time and pattern to an alarm, such as an alarm indicating the quality of electrode signals, patient compliance with device use and wear requirements, and/or a battery level, detected by the sensor interface 312. For example, for a certain period of time (e.g., 2 weeks) or a number of electrode-related events, the controller 120 can analyze historical information relating to average response to such alarms. If the patient takes on average more than a threshold period of time to respond to the alarms, e.g., about 1 minute to respond, the controller 120 can adapt the alarms to be louder, or more frequent, or to provide a voice command to guide the patient. Similarly, the controller 120 can learn patient response time and pattern to an alarm concerning arrhythmia for a certain period of time (e.g., 2 weeks) or a number of events, and the controller 120 can analyze historical information relating to patient average response time. If the patient takes on average more than a threshold period of time to respond to the alarm, the alarm can be adapted to be louder, or more frequent, or adapted to provide voice commands to guide the patient.

In some examples, the controller 120 can analyze a patient's response pattern to particular alarms including how a patient responds to the particular alert. For example, if the controller 120 determines that the patient is frequently performing a wrong action in response to an alarm, such as, pressing the physical response buttons instead of responding to a notification through the touch screen 220, the controller 120 can adjust the patient interaction mode to provide a voice command guiding the patient through the appropriate response and/or action. In another example, the device can be configured to comprise various alarm levels or intensities (e.g., gong alarms and siren alarms). The patient can be instructed to respond to different alarms in different ways. For example, the patient can be instructed to immediately press a response button to delay or cancel treatment when the device emits a siren alarm. In contrast, the patient can be instructed to read and follow on screen instructions when the device emits the lower intensity gong alarm. If the patient responds to a gong alarm by pressing the response buttons and/or to a siren alarm by pressing the display touch screen rather than the response buttons, the device can record or flag such actions as instances of incorrect use of the device. If multiple instances of incorrect use of the device are identified, the controller 120 can determine that the patient interaction mode should be adjusted, e.g., to include additional instructions to help the patient differentiate between different types of alarms and for how to respond to the different alarm types or to include only critical types of alarms so that the patient is not confused by different types of alarms.

In an example, if the controller 120 determines that the external medical device 100 is emitting an abnormally high number of alarms, e.g., above a threshold number, the controller 120 can provide a prompt to the patient to call technical support. In another example, the controller 120 can analyze the ECG data of the patient and adjust the alarm threshold for issuing alarms for medical events, such as ventricular fibrillation. For example, if the controller 120 has a threshold heart rate of 120-200 beats per minute for determine ventricular fibrillation in the patient, the controller 120 can adjust the threshold if it is determined over a period of time that the patient's typical heart rate, e.g., a heart rate of the patient when the patient's other physiological parameters are otherwise acceptable, is outside the threshold range in order to reduce the number of false alarms.

In another example, the controller 120 can determine that an ability of the patient to operate the external medical device 100 has improved over time, for example, by providing follow-up tests to the patient, and unlock a more advanced mode or additional features in a custom mode for the patient. For example, a patient originally assigned a device with the second technology comfort level mode can become more familiar with more basic features and functions of the device over time. The controller 120 can determine based on the patient's input to follow-up tests that the patient's technology comfort level has increased or that a cognitive level of the patient improved, e.g., in response to receiving a new medication or treatment, and adjust the second technology comfort mode to the first technology comfort mode or adjust one or more features in a custom technology comfort mode to provide the patient with access to more features and function of the device.

Assess for Pinch Strength

According to an aspect of the disclosure, the medical device disclosed herein can be configured to measure pinch strength (e.g., patient's fingertip pinch force), since identified changes in pinch strength may parallel hand force and grip strength changes. As such, detected changes in pinch strength can be used by caregivers or physicians to draw conclusions about patient condition and/or patient mortality (e.g., cardiovascular mortality). In this way, pinch strength can be used as a simple, quick, and inexpensive indicator of patient cardiovascular condition. For most patients, pinch strength is fairly stable, following similar patterns from about age 20 through age 60 or 65. Pinch strength then often diminishes slowly to about age 75. Pinch strength is generally not effected by whether the patient is right- or left-handed. In some cases, the less dominant hand may actually be stronger. However, some studies suggest that pinch strength may be affected by menopause, carpal tunnel, and arthritis, among other conditions.

In one example, the medical device can include buttons associated or embedded with force or pressure sensors for measuring the amount of force that the patient is capable of exerting on the buttons. Patient pinch strength can be measured each time the user presses the buttons. In other examples, the patient may be instructed to perform a "pinch test" by pressing and holding the buttons for a predetermined duration.

In some implementations, the medical device can be configured to test different types of pinch strength. For example, 2-point, 3-point, and key pinch may be tested. 2-point pinch is a force exerted between the tip of the thumb and index finger, as occurs when the patient presses the response buttons in a standard fashion. 2-point pinch tends to be the weakest of the types of pinches. Average 2-point pinch force for a male age 20-50 is between about 20 lbs. and 22 lbs. The 2-point pinch force declines about 20% to 24% from the average pinch force value at age 75 and about 40% from the average at age 85. Average 2-point pinch force for a female age 20-50 is about 10-14 lbs. The pinch force declines about 25% from the average at age 75 and about 40% from average at age 85. 3-point pinch is a force exerted between the pad of the thumb and the pads of the index and middle fingers. The 3-point pinch is typically about 30% stronger than the 2-point pinch. Average 3-point pinch force for a male age 20-50 is about 23 lbs. The pinch force declines to about 18 lbs. from the average for individuals that are 75 and older. Average 3-point pinch force for a female is about 16 lbs. for age 20-50. The pinch force declines to about 12 lbs. for individuals that are 75 and older. Key pinch is between the pad of the thumb and the medial-lateral surface of the index finger, as occurs when holding a key. Key pinch is also stronger than the 2-point pinch. Average key pinch force is about 22 lbs. to 27 lbs. for males ages 20-50, which declines to about 20 lbs. for individuals age 75 and older. Average key pinch force is about 16 lbs. for females age 20-50, which declines to about 12 lbs. for individuals age 75 and older.

In some examples, the device can instruct the patient to perform the pinch test daily, weekly, or according to another predetermined schedule. In some examples, pinch force may be measured several times in quick succession to determine an average pinch force value. The measured average pinch force, measured several consecutive times, can be compared with a patient's established baseline, which is measured when the patient is fitted with the device, to identify when a clinically significant change in pinch force occurs. For example, a physician may program upper and lower limits for pinch force. Measured pinch force outside of the identified limits may trigger an alert. For example, the physician may set a threshold of 2 kg (4.4 lbs.). If measured pinch force differs from a patient's baseline or normal pinch force by more than 2 kg, the alarm may be triggered and the caregiver or physician notified. However, threshold values are generally left to the discretion of the responsible physician. A threshold value of 2 kg is merely an example of a value which a physician may select. Other threshold values may also be selected within the scope of the present disclosure.

The medical device may also be configured to track changes in a patient's pinch strength over time to detect sustained changes which could point to deterioration of patient condition. In a similar manner, in some instances, pinch force measurements for one or more patients can be measured and correlated with other patient data (e.g., patient condition information, mortality information, cardiac function information) to produce a database of pinch force measurements and patient outcomes. The database can be updated as additional data is collected and can be used to improve predication accuracy and/or specificity.

In some implementations, the device can be configured to identify when a pinch force is asymmetrical (e.g., when the patient applies a greater force to one response button than to the other). Unequal pinch forces may suggest that the patient is experiencing problems with the hands or fingers, such as a worsening flexibility or strength issue. Instances of unequal pinch force may be monitored and reported to the physician. For example, the physician may set up parameters or threshold values for how much difference between fingers is tolerated. For example, the physician may ask to be notified if there is more than a 20% or 2 kg (4.4 lbs) difference between readings from the two response buttons. Other threshold values or ranges of threshold values may also be selected by the responsible physician or caregiver based on particular patient requirements and/or personal preference within the scope of the present disclosure.

As shown in FIG. 11, a controller 120 configured to monitor the patient's pinch strength based on information received from force or pressure sensors 612 associated with or embedded on buttons, such as the response buttons 210, is illustrated. The pressure sensors 612 can be any of a variety of force sensors. One such example is a piezo-resistive force sensor with an operating range of 0-30 lbs. (13.6 kg), such as the FlexiForce sensors manufactured by Tekscan (https://www.tekscan.com/product-group/embedded-sensing/force-sensors). In some examples, patient pinch strength can be measured and recorded each time that the patient presses the response buttons 210. In other examples, the patient may be periodically prompted to perform a pinch test to obtain a pinch strength measurement.

During a pinch test, the patient can be prompted to press the response buttons 210 of the controller 120. For example, the patient may place his/her thumb on the response button 210 on one side of the controller 120 and his/her index or middle finger on the response button 210 on the other side of the controller 120. When instructed by the controller 120 to begin the test, the patient presses the buttons 210 in a pinching motion. For example, the patient may press and hold the buttons 210 until a release signal, such as a beep or tactile sensation, is emitted from the controller 120. As the patient presses the buttons 210, the pressure sensors 612 measure force exerted on the buttons 210 by the patient's fingers.

In some examples, signals representative of the force or pressure measurements are provided from the controller 120 to an external computing device 610, such as a laptop computer, smart phone, tablet, or personal digital assistant. In other examples, the processing techniques discussed herein may be performed on the controller 120 and results can be transmitted to the external computing device 610. In some examples, the external computing device 610 can include circuitry, such as a force amplifier 614, along with other processors or controllers, which process signals from the pressure sensors 612 to determine a pinch force measurement. The pinch force measurement is provided from the force amplifier 614 to electronic circuitry, such as a comparator 616, for comparing the pinch force measurements to other values. For example, the comparator 616 can be configured to analyze the pinch force measurements by comparing the pinch force values to various reference values. In some instances, the comparator 616 can be configured to receive the reference values from a database 618 of previous pinch force measurements to assess changes in the patient's pinch strength over time.

For example, the database 618 can include previous pinch force measurements for the patient taken at periodic intervals over the previous day or week. A trend representative of a decrease in pinch strength over time may indicate that the patient's condition is deteriorating. The database 618 can also include baseline values for the patient and/or reference pinch force values for individuals with similar physical characteristics (e.g., gender, age, height, weight, and occupation) as the patient. A determination that a patient has a lower than expected pinch force, compared to other individuals with similar physical characteristics, may indicate that the patient is suffering from an undiagnosed injury or condition.

As shown in FIG. 11, results of the comparison between a measured pinch force and previously measured pinch force values can be evaluated with a decision algorithm module 620 of the external computing device 610. The decision algorithm module 620 can be configured to receive and analyze information from the comparator 616 based on received programmable thresholds 621. In some examples, analysis of changes in patient condition can be provided from the decision algorithm module 620 to a user interface module 622. The user interface module 622 can include an audio or visual feedback device for providing information to a user. For example, a feedback device may display a notification or alert based on identified changes in the patient's condition. In some instances, the notification or alert can instruct the patient to seek emergency medical treatment or to contact his/her physician or care provider. The user interface module 622 can also cause the patient condition information to be wirelessly transmitted to an external source, such as a patient care network or for inclusion in the patient's electronic health record. In a similar manner, as shown at box 624, pinch force measurements and/or predictions regarding patient condition can be provided to the patient's physician and/or caregiver in the form of a patient report. The physician or caregiver can review the pinch force measurement results along with other measurements related to patient condition and make decisions about an appropriate course of treatment for the patient.

The embodiments have been described with reference to various examples. Modifications and alterations will occur to others upon reading and understanding the foregoing examples. Accordingly, the foregoing examples are not to be construed as limiting the disclosure.

What is claimed is:

1. A wearable monitoring and treatment device for automatically changing how a patient interacts with the device, the device comprising:
 a garment configured to be worn on a torso of the patient;
 a shock generator supported by the garment and configured to generate an electrical therapeutic shock;
 a plurality of therapy and/or sensing electrodes disposed within the garment and operatively connected to the shock generator configured to monitor an ECG of the patient and/or deliver the electrical therapeutic shock to the patient;
 a monitor configured to be operationally coupled to the garment, the monitor comprising a user interface configured to allow the patient to perform predetermined one or more requested response actions in response to one or more prompts from the device, wherein the one or more prompts are generated by the monitor based on signals detected by one or more of the plurality of therapy and/or sensing electrodes; and
 a controller operatively connected to the user interface and the shock generator, wherein the controller is configured to:
  initiate an initial patient interaction mode of the device, wherein the initial patient interaction mode comprises the predetermined one or more requested response actions in response to the one or more prompts from the device,
  receive, via the user interface, patient input to the one or more prompts from the device, and
  modify, based on the patient input, the initial patient interaction mode to a modified patient interaction mode comprising a modified predetermined one or more requested response actions to be performed in response to the one or more prompts from the device.

2. The device of claim 1, wherein the electrical therapeutic shock delivered to the patient by the plurality of therapy electrodes comprises at least one of a therapeutic defibrillation shock, pacing pulses, and/or TENS pulses.

3. The device of claim 1, wherein the monitor further comprises at least one response button, and wherein the one or more requested response actions of the initial patient interaction mode comprises pressing the at least one response button.

4. The device of claim 1, further comprising a user interface pod separate from the monitor in wired or wireless communication with the monitor, wherein the user interface pod comprises at least one response button, and wherein the one or more requested response actions of the initial patient interaction mode comprises pressing the at least one response button of the user interface pod.

5. The device of claim 4, wherein the user interface pod further comprises a speaker that provides the one or more prompts of the initial patient interaction mode.

6. The device of claim 1, wherein the user interface comprises a touch screen display, and wherein the one or more prompts are displayed on the touch screen display.

7. The device of claim 1, wherein the controller is further configured to:
 identify a patient event treatable by the electrical therapeutic shock based, at least in part, on the monitored ECG of the patient;
 upon detection of the patient event, cause the device to issue the one or more prompts from the device of the initial patient interaction mode or of the modified patient interaction mode; and
 suspend generation of the electrical therapeutic shock when one of the one or more requested response actions is performed by the patient.

8. The device of claim 7, wherein the controller is further configured to cause the shock generator to deliver the electrical therapeutic shock to the patient when one of the one or more requested response actions is not performed by the patient within a predetermined period of time.

9. The device of claim 1, wherein the one or more requested response actions of the initial patient interaction mode and/or of the modified patient interaction mode are selected from a plurality of possible requested response actions based on at least one of the patient's ability, function, and/or skill.

10. The device of claim 1, wherein the one or more prompts of the initial patient interaction mode are output by one of a visual display, an audio output, or a tactile output of the device, and the one or more prompts of the modified patient interaction mode are output by another of the visual display, an audio output, or a tactile output of the device.

11. The device of claim 1, wherein modifying the initial patient interaction mode to the modified patient interaction mode comprises changing at least one of: a) an order or a sequence of the one or more prompts from the device, b) a type of the one or more prompts of the device, c) a frequency of occurrence of the one or more prompts of the device, and/or d) an escalation pattern of the one or more prompts of the device.

12. The device of claim 1, wherein the initial patient interaction mode and/or the modified patient interaction mode is one of: a) a first technology comfort mode, b) a second technology comfort mode, and/or c) a custom technology comfort mode.

13. The device of claim 12, wherein the first technology comfort mode is characterized by having predominantly more textual elements on the touch screen of the wearable monitoring and treatment device than the second technology comfort mode, and
wherein the second technology comfort mode is characterized by having predominantly more image, animation, or video based elements on the touch screen display than the first technology comfort mode.

14. A wearable monitoring and treatment device for automatically changing how a patient interacts with the device, the device comprising:
a garment configured to be worn on a torso of the patient;
a shock generator supported by the garment and configured to generate an electrical therapeutic shock;
a plurality of therapy and/or sensing electrodes disposed within the garment and operatively connected to the shock generator configured to monitor an ECG of the patient and/or deliver the electrical therapeutic shock to the patient;
a monitor configured to be operationally coupled to the garment, the monitor comprising a user interface configured to allow the patient to perform predetermined one or more requested response actions in response to one or more prompts from the device, wherein the one or more prompts comprise alarms provided by the device informing the patient that the electrical therapeutic shock will be generated; and
a controller operatively connected to the user interface and the shock generator, wherein the controller is configured to:
initiate an initial patient interaction mode of the device, wherein the initial patient interaction mode comprises the predetermined one or more requested response actions in response to the one or more prompts from the device,
receive, via the user interface, patient input to the one or more prompts from the device, and
modify, based on the patient input, the initial patient interaction mode to a modified patient interaction mode comprising a modified predetermined one or more requested response actions to be performed in response to the one or more prompts from the device.

15. The device of claim 14, wherein the electrical therapeutic shock delivered to the patient by the plurality of therapy electrodes comprises at least one of a defibrillation shock or pacing pulses.

16. The device of claim 14, wherein the user interface comprises a touch screen display, and wherein the one or more prompts are displayed on the touch screen display.

17. The device of claim 14, wherein the controller is further configured to:
identify a patient event treatable by the electrical therapeutic shock based, at least in part, on the monitored ECG of the patient;
upon detection of the patient event, cause the device to issue the one or more prompts from the device of the initial patient interaction mode or of the modified patient interaction mode; and
suspend generation of the electrical therapeutic shock when one of the one or more requested response actions is performed by the patient.

18. The device of claim 17, wherein the controller is further configured to cause the shock generator to deliver the electrical therapeutic shock to the patient when one of the one or more requested response actions is not performed by the patient within a predetermined period of time.

19. The device of claim 14, wherein the monitor further comprises a plurality of response buttons, the one or more requested response actions of the initial patient interaction mode comprises simultaneously pressing at least two of the plurality of response buttons, and the modified patient interaction mode comprises pressing at least one of the plurality of response buttons.

20. The device of claim 14, wherein the one or more prompts of the initial patient interaction mode are output by one of a visual display, an audio output, or a tactile output of the device, and the one or more prompts of the modified patient interaction mode are output by another of the visual display, an audio output, or a tactile output of the device.

21. A wearable monitoring and treatment device for automatically changing how a patient interacts with the device, the device comprising:
a garment configured to be worn on a torso of the patient;
a shock generator supported by the garment and configured to generate an electrical therapeutic shock;
a plurality of therapy and/or sensing electrodes disposed within the garment and operatively connected to the shock generator configured to monitor an ECG of the patient and/or deliver the electrical therapeutic shock to the patient;
a monitor configured to be operationally coupled to the garment, the monitor comprising a user interface configured to allow the patient to perform predetermined one or more requested response actions in response to one or more prompts from the device, wherein the one or more requested response actions of the initial patient interaction mode comprise at least one of: pressing at least one response button of the wearable monitoring and treatment device, simultaneously pressing at least two response buttons of the wearable monitoring and treatment device, touching a virtual element on a touch screen display of the user interface, or speaking a predetermined word or phrase that can be recorded by an audio sensor of the monitor, and
a controller operatively connected to the user interface and the shock generator, wherein the controller is configured to:
initiate an initial patient interaction mode of the device, wherein the initial patient interaction mode comprises the predetermined one or more requested response actions in response to the one or more prompts from the device, receive, via the user interface, patient input to the one or more prompts from the device, and modify, based on the patient input, the initial patient interaction mode to a modified patient interaction mode by changing the requested response action to another of the one or more response actions.

22. The device of claim 21, wherein the one or more prompts from the device of the initial patient interaction mode comprise questions of a test provided to the patient to assess ability of the patient, and wherein the received patient input comprises answers to the questions.

23. The device of claim 22, wherein the test provided to the patient comprises at least one of an inductive reasoning test, an intelligence quotient test, a situation judgment test, a working memory test, a psychomotor ability test, a language test, a technology ability test, a color blindness test, a hearing test, a vision test, a steadiness test, and a movement test.

24. The device of claim 22, wherein the test comprises a predetermined series of prompts provided to the patient during the patient's initial interaction with the device, and wherein the received patient input comprises responses to the series of prompts.

25. The device of claim 22, wherein the controller is configured to provide the test to the patient on a periodic basis.

26. The device of claim 22, wherein the controller is configured to provide the test to the patient at times determined in response to patient interaction with the device.

* * * * *